US006159462A

United States Patent [19]
Matthews et al.

[11] Patent Number: 6,159,462
[45] Date of Patent: *Dec. 12, 2000

[54] USES OF WNT POLYPEPTIDES

[75] Inventors: William Matthews, Woodside; Timothy W. Austin, Morgan Hill, both of Calif.

[73] Assignee: Genentech, Inc., So. San Francisco, Calif.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/911,860

[22] Filed: Aug. 15, 1997

Related U.S. Application Data

[60] Provisional application No. 60/024,068, Aug. 16, 1996.

[51] Int. Cl.[7] .............................. A61K 45/05; C12N 5/02; A01N 37/18; C07K 1/00
[52] U.S. Cl. ...................... 424/85.1; 424/85.2; 435/383; 435/395; 435/404; 435/405; 435/406; 514/2; 514/814; 530/350; 530/351; 530/868
[58] Field of Search ..................... 530/350, 351, 530/868; 514/2, 814; 424/85.1, 85.2; 435/383, 395, 404, 405, 406

[56] References Cited

U.S. PATENT DOCUMENTS

| | | |
|---|---|---|
| Re. 30,985 | 6/1982 | Cartaya . |
| 3,691,016 | 9/1972 | Patel . |
| 3,773,919 | 11/1973 | Boswell . |
| 3,969,287 | 7/1976 | Jaworek et al. . |
| 4,002,531 | 1/1977 | Royer . |
| 4,179,337 | 12/1979 | Davis et al. . |
| 4,195,128 | 3/1980 | Hildebrand et al. . |
| 4,229,537 | 10/1980 | Hodgins et al. . |
| 4,247,642 | 1/1981 | Hirohara et al. . |
| 4,275,149 | 6/1981 | Litman et al. . |
| 4,301,144 | 11/1981 | Iwashita et al. . |
| 4,330,440 | 5/1982 | Ayers et al. . |
| 4,376,110 | 3/1983 | David et al. . |
| 4,399,216 | 8/1983 | Axel et al. . |
| 4,419,446 | 12/1983 | Howley et al. . |
| 4,496,689 | 1/1985 | Mitra . |
| 4,544,545 | 10/1985 | Ryan et al. . |
| 4,560,655 | 12/1985 | Baker . |
| 4,601,978 | 7/1986 | Karin . |
| 4,640,835 | 2/1987 | Shimizu et al. . |
| 4,657,866 | 4/1987 | Kumar . |
| 4,670,417 | 6/1987 | Iwasaki et al. . |
| 4,676,980 | 6/1987 | Segal et al. . |
| 4,767,704 | 8/1988 | Cleveland et al. . |
| 4,791,192 | 12/1988 | Nakagawa et al. . |
| 4,816,567 | 3/1989 | Cabilly et al. . |
| 4,927,762 | 5/1990 | Darfler . |
| 4,943,529 | 7/1990 | Van den Berg et al. . |
| 4,946,783 | 8/1990 | Beckwith et al. . |
| 4,965,199 | 10/1990 | Capon et al. . |
| 5,010,182 | 4/1991 | Brake et al. . |
| 5,013,556 | 5/1991 | Woodle et al. . |
| 5,122,469 | 6/1992 | Mather et al. . |
| 5,364,934 | 11/1994 | Drayna et al. . |
| 5,851,984 | 12/1998 | Matthews et al. ................. 514/2 |

FOREIGN PATENT DOCUMENTS

| | | |
|---|---|---|
| 003089 | 7/1979 | European Pat. Off. . |
| 036776 | 9/1981 | European Pat. Off. . |
| 073657 | 3/1983 | European Pat. Off. . |
| 117058 | 8/1984 | European Pat. Off. . |
| 117060 | 8/1984 | European Pat. Off. . |
| 139383 | 5/1985 | European Pat. Off. . |
| 183070 | 6/1986 | European Pat. Off. . |
| 244234 | 11/1987 | European Pat. Off. . |
| 307247 | 3/1989 | European Pat. Off. . |
| 321196 | 6/1989 | European Pat. Off. . |
| 362179 | 4/1990 | European Pat. Off. . |
| 394538 | 10/1990 | European Pat. Off. . |
| 402226 | 12/1990 | European Pat. Off. . |
| 266710 | 4/1989 | Germany . |
| 2211504 | 7/1989 | United Kingdom . |

(List continued on next page.)

OTHER PUBLICATIONS

Bradley, RS et al. Molec. Cell Biol. 15(8):4616–4622, Aug. 1995.

*Tissue Culture,* Kruse and Patterson, eds., New York:Academic Press (1973).

*Mammalian Cell Biotechnology: A Practical Approach,* M. Butler, ed., IRL Press (1991).

*Remington's Pharmaceutical Sciences,* Oslo et al., eds., 16th edition, Mack Publishing Co. (1980).

Al–Mashikhi et al., "Separation of immunoglobulin and transferrin from blood serum and plasma by metal chelate interaction chromatography", *J. Dairy Sci.* 71:1756–1763 (1988).

Anderson et al., "Molecular cloning of mast cell growth factor, a hematopoietin that is active in both membrane bound and soluble forms" *Cell* 63:235–243 (1990).

Anderson, W.F., "Human gene therapy" *Science* 256:808–813 (1992).

Aplin et al., "Preparation, Properties, and Applications of Carbohydrate Conjugates of Proteins and Lipids" *CRC Crit. Rev. Biochem.* 10(4):259–305 (1981).

Aruffo et al., "CD44 is the Principal Cell Surface Receptor for Hyaluronate" *Cell* 61:1303–1313 (Jun. 29, 1990).

Ashkenazi et al., "Protection Against Endotoxic Shock by a Tumor Necrosis Factor Receptor Immunoadhesin" *Proc. Natl. Acad. Sci.* 88:10535–10539 (1991).

Austin et al., "A Role for the Wnt Gene Family in Hematopoiesis: Expansion of Multilineage Progenitor Cells" *Blood* 89(10):3624–3635 (May 15, 1997).

(List continued on next page.)

*Primary Examiner*—David Saunders
*Assistant Examiner*—F. Pierre VanderVegt
*Attorney, Agent, or Firm*—Craig G. Svoboda; David A. Carpenter

[57] ABSTRACT

Uses for Wnt polypeptides in hematopoiesis are disclosed. In particular, in vitro and in vivo methods for enhancing proliferation, differentiation or maintenance of a hematopoietic stem/progenitor cell using a Wnt polypeptide, and optionally another cytokine, are described.

13 Claims, 2 Drawing Sheets

FOREIGN PATENT DOCUMENTS

| | | |
|---|---|---|
| WO 87/00195 | 1/1987 | WIPO . |
| WO 87/05330 | 9/1987 | WIPO . |
| WO 89/05859 | 6/1989 | WIPO . |
| WO 90/03430 | 4/1990 | WIPO . |
| WO 90/13646 | 11/1990 | WIPO . |
| WO 91/00357 | 1/1991 | WIPO . |
| WO 91/00358 | 1/1991 | WIPO . |
| WO 91/00360 | 1/1991 | WIPO . |
| WO 91/08291 | 6/1991 | WIPO . |
| WO 91/08298 | 6/1991 | WIPO . |
| WO 92/20373 | 11/1992 | WIPO . |
| WO 93/08829 | 5/1993 | WIPO . |
| WO 94/02157 | 2/1994 | WIPO . |
| WO 94/04690 | 3/1994 | WIPO . |
| WO 94/14708 | 7/1994 | WIPO . |
| WO 95/17416 | 6/1995 | WIPO . |
| WO 95/27062 | 10/1995 | WIPO . |

OTHER PUBLICATIONS

Baker, N., "Embryonic and imaginal requirements for wingless, a segment–polarity gene in Drosophila" *Dev. Biol.* 125:96–108 (1988).

Ballance et al., "Transformation of *Aspergillus Nidulans* by the Orotidine–5'–phosphate Decarboxylase Gene of Neurospora Crassa" *Biochem. & Biophys. Res. Comm.* 112(1):284–289 (Apr. 15, 1983).

Banergji et al., "A Lymphocyte–specific Cellular Enhancer Is Located Downstream of the Joining Region in Immunoglobulin Heavy Chain Genes" *Cell* 33:729–740 (Jul. 1983).

Barnes et al., "Methods for Growth of Cultured Cells in Serum–free Medium" *Analytical Biochemistry* 102:255–270 (1980).

Bayer et al., "The avidin–biotin complex in affinity cytochemistry" *Methods in Enzymology* 62:308–315 (1979).

Beach et al., "High–Frequencey Transformation of the Fission Yeast *Schizosaccharomyces Pombe*" *Nature* 290:140–142 (Mar. 12, 1981).

Beauchamp et al., "A new procedure for the synthesis of polyethylene glycol–protein adducts; effects on function, receptor recognition, and clearance of superoxide dismutase, lactoferrin, and alpha 2–macroglobulin" *Analytical Biochemistry* 131(1):25–33 (1983).

Bennett et al., "Extracellular Domain–IgG Fusion Proteins for Three Human Natriuretic Peptide Receptors. Hormone Pharmacology and Application to Solid Phase Screening of Synthetic Peptide Antisera" *The Journal of Biological Chemistry* 266(34):23060–23067 (Dec. 5, 1991).

Bianchi et al., "Transformation of the yeast *Kluyveromyces lactis* by New Vectors Derived from the 1.6 $\mu$m Circular Plasmid pKD1" *Curr. Genet.* 12:185–192 (1987).

Bodine et al., "Effects of hematopoietic growth factors on the survival of primitive stem cells in liquid suspension culture" *Blood* 78:914–920 (1991).

Boggs et al., "Hematopoietic stem cells with high proliferative potential. Assay of their concentration in marrow by the frequency and duration of cure of W/Wv mice" *J. Clin. Inv.* 70(2):242–253 (1982).

Bradbury et al., "Wnt–4 expression induces a pregnancy––like growth pattern in reconstituted mammary glands in virgin mice" *Dev. Biol.* 170:553–563 (1995).

Bradley and Brown, "The proto–oncogene int–1 encodes a secreted protein associated with the extracellular matrix" *EMBO Journal* 9:1569–1575 (1990).

Brodeur et al., "Mouse–Human Myeloma Partners for the Production of Heterohybridomas" *Monoclonal Antibody Production Techniques and Applications,* New York:Marcel Dekker, Inc. pp. 51–63 (1987).

Bruggemann et al., "Designer Mice: The Production of Human Antibody Repertoires in Transgenic Animals" *Year in Immunology* 7:33–40 (1993).

Byrn et al., "Biological Properties of a CD4 Immunoadhesin" *Nature* 344:667–670 (Apr. 12, 1990).

Canaani et al., "Regulated Expression of Human Interferon $\beta_1$ Gene After Transduction into Cultured Mouse and Rabbit Cells" *Proc. Natl. Acad. Sci. USA* 79:5166–5170 (Sep. 1982).

Capon et al., "Designing CD4 Immunoadhesins for AIDS Therapy" *Nature* 337:525–531 (Feb. 9, 1989).

Carter et al., "Humanization of an anti–p185$^{HER2}$ antibody for human cancer therapy" *Proc. Natl. Acad. Sci.* 89:4285–4289 (1992).

Case et al., "Efficient Transformation of Neurospora Crassa by Utilizing Hybrid Plasmid DNA" *Proc. Natl. Acad. Sci.* 76(10):5259–5263 (Oct. 1979).

Chang et al., "Phenotypic Expression in *E. coli* of a DNA Sequence Coding for Mouse Dihydrofolate Reductase" *Nature* 275:617–624 (Oct. 19, 1978).

Chothia and Lesk, "Canonical structures for the hypervariable regions of immunoglobulins" *J. Mol. Biol.* 196(4):901–917 (1987).

Christian and Moon, "Interactions between Xwnt–8 and Spemann organizer signaling pathways generate dorsoventral pattern in the embryonic mesoderm of Xenopus" *Genes Dev.* 7:13–28 (1993).

Christian and Moon, "When cells take fate into their own hands: differential competence to respond to inducing signals generates diversity in the embryonic mesoderm" *Bio Essays* 15(2):135–140 (1993).

Christiansen et al., "Murine Wnt–11 and Wnt–12 have temporally and spatially restricted expression patterns during embryonic development" *Mech. Dev.* 51(2–3):341–350 (1995).

Clackson et al., "Making antibody fragments using phage display libraries" *Nature* 352:624–628 (1991).

Cooke, J., "Induction and All That" *Nature* 358:111–112 (1992).

Creighton, T.E. *Proteins: Structure and Molecular Properties,* W.H. Freeman & Co.: San Francisco pp. 79–86 (1983).

David et al., "Protein Iodination with Solid State Lactoperoxidase" *Biochemistry* 13(5):1014–1021 (1974).

deBoer et al., "The TAC Promoter: A functional Hybrid Derived From the TRP and LAC Promoters" *Proc. Natl. Acad. Sci. USA* 80:21–25 (1983).

Depicker et al., "Nopaline Synthase: Transcript Mapping and DNA Sequence" *J. Mol. Appl. Gen.* 1:561–573 (1982).

Dexter et al., "Growth and Differentiation in the Hemopoietic System" *Ann. Rev. Cell Biol.* 3:423–441 (1987).

Duksin et al., "Relationship of the Structure and Biological Activity of the Natural Homologues of Tunicamycin" *Journal of Biological Chemistry* 257:3105–3109 (1982).

Dzau et al., "Gene therapy for cardiovascular disease" *Trends in Biotechnology* 11:205–210 (1993).

Dzierzak and Medvinsky, "Mouse embryonic hematopoiesis" *Trends Genet.* 11:359–366 (1995).

Edge et al., "Deglycosylation of glycoproteins by trifluoromethanesulfonic acid" *Analytical Biochemistry* 118:131–137 (1981).

Eppstein et al., "Biological Activity of Liposome–Encapsulated Murine Interferon Gamma Is Mediated by a Cell Membrane Receptor" *Proc. Natl. Acad. Sci.* 82(11):3688–3692 (1985).

Evan et al., "Isolation of Monoclonal Antibodies Specific for Human c–myc Proto–Oncogene Product" *Molecular & Cellular Biology* 5:3610–3616 (1985).

Field et al., "Purification of a RAS–Responsive Adenylyl Cyclase Complex from *Saccharomyces cerevisiae* by Use of an Epitope Addition Method" *Molecular & Cellular Biology* 8:2159–2165 (1988).

Fiering et al., "Improved FACS–Gal: flow cytometric analysis and sorting of viable eukaryotic cells expressing reporter gene constructs" *Cytometry* 12:291–301 (1991).

Fiers et al., "Complete Nucleotide Sequence of SV40 DNA" *Nature* 273:113–120 (May 11, 1978).

Fleer et al., "Stable Multicopy Vectors for High–Level Secretion of Recombinant Human Serum Albumin by Kluyveromyces Yeasts" *Bio/Technology* 9:968–975 (1991).

Fraser et al., "Proliferation of totipotent hematopoietic stem cells in vitro with retention of long–term competitive in vivo reconstituting ability" *Proc. Natl. Acad. Sci.* 89:1968–1972 (1992).

Gascoigne et al., "Secretion of a Chimeric T–cell Receptor–immunoglobulin Protein" *Proc. Natl. Acad. Sci. USA* 84:2936–2940 (1987).

Gavin et al., "Expression of multiple novel Wnt–1/int–1–related genes during fetal and adult mouse development" *Genes Dev.* 4:2319–2332 (1990).

Gerard et al., "A Rapid and Quantitative Assay to Estimate Gene–Transfer Into Retrovirally Transduced Hematopoietic Stem Progenitor Cells Using a 96–Well Format PCR and Fluorescent Detection System Universal for MMLV–Based Proviruses" *Human Gene Therapy* 7(3):343–354 (1996).

Gething et al., "Cell–surface Expression of Influenza Haemagglutinin from a Cloned DNA Copy of the RNA Gene" *Nature* 293:620–625 (Oct. 22, 1981).

Ghattas et al., "The encephalomyocarditis virus internal ribosome entry site allows efficient coexpression of two genes from a recombinant provirus in cultured cells and in embryos" *Molecular & Cellular Biology* 11:5848–5859 (1991).

Goding, "Production of Monoclonal Antibodies" *Monoclonal Antibodies: Principles and Practice,* Academic Press, pp. 59–103 (1986).

Goeddel et al., "Direct Expression in *Escherichia coli* of a DNA Sequence Coding for Human Growth Hormone" *Nature* 281:544–548 (Oct. 18, 1979).

Goeddel et al., "Synthesis of Human Fibroblast Interferon by *E. coli*" *Nucleic Acids Research* 8(18):4057–4074 (1980).

Gorman et al., "The Rous Sarcoma Virus Long Terminal Repeat is a Strong Promoter When Introduced into a Variety of Eukaryotic Cells by DNA–Mediated Transfection" *Proc. Natl. Acad. Sci. USA* 79:6777–6781 (Nov. 1982).

Gorman, C., "High Efficiency Gene Transfer Into Mammalian Cells" *DNA Cloning: A Practical Approach,* Glover, D.M., ed, Washington D.C.:IRL Press vol. 2:143–190 (1985).

Graham et al., "Characteristics of a Human Cell Line Transformed by DNA from human Adenovirus Type 5" *J. Gen. Virol.* 36:59–72 (1977).

Graham et al., "A New Technique for the Assay of Infectivity of Human Adenovirus 5 DNA" *Virology* 52:456–467 (1973).

Gray et al., "Expression of Human Immune Interferon cDNA in *E. coli* and Monkey Cells" *Nature* 295:503–508 (Feb. 11, 1982).

Greenaway et al., "Human Cytomegalovirus DNA: BamHI, EcoRI and PstI Restriction Endonuclease Cleavage Maps" *Gene* 18:355–360 (1982).

Gruber et al., "Efficient Tumor Cell Lysis Mediated by a Bispecific Single Chain Antibody Expressed in *Escherichia Coli*" *Journal of Immunology* 152:5368–5374 (1994).

Guss et al., "Structure of the IgG–binding regions of streptococcal protein G" *EMBO Journal* 5:1567–1575 (1986).

Ham et al., "Media and Growth Requirements" *Methods in Enzymology* 58:44–93 (1979).

Harris et al., "Synthesis and Characterization of Poly(Ethylene Glycol) Derivatives" *J. Polym. Sci., Polym. Chem. Ed.* 22(2):341–352 (1984).

Harrison et al., "Number and continuous proliferative pattern of transplanted primitive immunohematopoietic stem cells" *Proc. Natl. Acad. Sci.* 85(3):822–826 (1988).

Heitzmann et al., "Use of the avidin–biotin complex for specific staining of biological membranes in electron microscopy" *Proc. Natl. Acad. Sci.* 71:3537–3541 (1974).

Hengen, P., "Purification of His–Tag fusion proteins from *Escherichia coli*" *Trends Biochem. Sci.* 20:285–286 (1995).

Herman and Horvitz, "The *Caenorhabditis elegans* gene lin–44 controls the polarity of asymmetric cell divisions" *Development* 120:1035–1047 (1994).

Hess et al., "Cooperation of Glycolytic Enzymes" *Advances in Enzyme Regulation,* George Weber, New York: Pergamon Press vol. 7:149–167 (1968).

Hinck et al., "Wnt–1 modulates cell–cell adhesion in mammalian cells by stabilizing beta–catenin binding to the cell adhesion protein cadherin" *Journal of Cell Biology* 124:729–741 (1994).

Hitzeman et al., "Isolation and Characterization of the Yeast 3–Phosphoglycerokinase Gene (PGK) by an Immunological Screening Technique" *Journal of Biological Chemistry* 255(24):12073–12080 (Dec. 25, 1980).

Holland et al., "Isolation and Identification of Yeast Messenger Ribonucleic Acids Coding for Enolase, Glyceraldehyde–3–phosphate Dehydrogenase, and Phosphoglycerate Kinase" *Biochemistry* 17(23):4900–4907 (1978).

Holliger et al., "Diabodies: Small bivalent and bispecific antibody fragments" *Proc. Natl. Acad. Sci. USA* 90:6444–6448 (1993).

Holmes et al., "Structure and Functional Expression of a Human Interleukin–8 Receptor" *Science* 253(5025):1278–1280 (Sep. 13, 1991).

Hoogenboom and Winter, "By–passing immunisation: human antibodies from synthetic repertoires of germline $V_H$ gene segments rearranged in vitro" *J. Mol. Biol.* 227:381–388 (1992).

Hoogenboom et al., "Construction and Expression of Antibody–Tumor Necrosis Factor Fusion Proteins" *Molecular Immunology* 28:1027–1037 (1991).

Hopp et al., "A Short Polypeptide Marker Sequence Useful for Recombinant Protein Identification and Purification" *Bio/Technology* 6:1204–1210 (1988).

Hsiao et al., "High–frequency Transformation of Yeast by Plasmids Containing the Cloned Yeast Arg4 Gene" *Proc. Natl. Acad. Sci. USA* 76:3829–3833 (1979).

Hus et al., "A Comparative Study of the Peroxidase–antiperoxidase Method and an Avidin–biotin Complex Method for Studying Polypeptide Hormones with Radioimmunoassay Antibodies" *Am. J. Clin. Path.* 75(5):734–738 (May 1981).

Hunter et al., "Preparation of Iodine 131 Labelled Human Growth Hormone of High Specific Activity" *Nature* 194:495–496 (1962).

Hutchens et al., "Thiophilic adsorption of immunoglobulins—analysis of conditions optimal for selective immobilization and purification" *Analytical Biochemistry* 159:217–226 (1986).

Hwang et al., "Hepatic uptake and degradation of unilamellar sphingomyelin/cholesterol liposomes: a kinetic study" *Proc. Natl. Acad. Sci.* 77:4030–4034 (1980).

Jakobovits et al., "Analysis of Homozygous Mutant Chimeric Mice: Deletion of the Immunoglobulin Heavy–Chain Joining Region Blocks B–cell Development and Antibody Production" *Proc. Natl. Acad. Sci. USA* 90:2551–2555 (Mar. 1993).

Jakobovits et al., "Germ–line Transmission and Expression of a Human–Derived Yeast Artificial Chromosome" *Nature* 362:255–258 (Mar. 18, 1993).

Jones et al., "Replacing the Complementarity–determining Regions in a Human Antibody with those From a Mouse" *Nature* 321:522–525 (May 29, 1986).

Jones, E., "Proteinase Mutants of *Saccharomyces Cerevisiae*" *Genetics* 85(1):23–33 (1977).

Kanatsu and Nishikawa, "In vitro analysis of epiblast tissue potency for hematopoietic cell differentiation" *Development* 122:823–830 (1996).

Kelly et al., "Transformation of *Aspergillus niger* by the amdS Gene of *Aspergillus nidulans*" *EMBO Journal* 4(2):475–479 (1985).

Keown et al., "Methods for Introducing DNA into Mammalian Cells" *Methods in Enzymology* 185:527–537 (1990).

Kessler and Melton, "Vertebrate embryonic induction: mesodermal and neural patterning" *Science* 266:596–604 (1994).

Klingensmith and Nusse, "Signaling by wingless in Drosophila" *Dev. Biol.* 166:396–414 (1994).

Kohler et al., "Continuous Cultures of Fused Cells Secreting Antibody of Predefined Specificity" *Nature* 256:495–497 (Aug. 7, 1975).

Kostelny et al., "Formation of a Bispecific Antibody by the Use of Leucine Zippers" *Journal of Immunology* 148(5):1547–1553 (1992).

Kozbor et al., "A Human Hybrid Myeloma for Production of Human Monoclonal Antibodies" *The Journal of Immunology* 133(6):3001–3005 (1984).

Ku and Melton, "Xwnt–11: a maternally expressed Xenopus wnt gene" *Development* 119:1161–1173 (1993).

Laimins et al., "Osmotic Control of kdp Operon Expression in *Escherichia Coli*" *Proc. Natl. Acad. Sci. USA* 78(1):464–468 (Jan. 1981).

Lee et al., "Insertional mutagenesis identifies a member of the Wnt gene family as a candidate oncogene in the mammary epithelium of int–2/Fgf–3 transgenic mice" *Proc. Natl. Acad. Sci.* 92(6):2268–2272 (1995).

Lesslauer, "Recombinant Soluble Tumor Necrosis Factor Receptor Proteins Protect Mice From Lipopolysaccharide–induced lethality" *European Journal of Immunology* 27:2883–2886 (1991).

Lindmark et al., "Binding of immunoglobulins to protein A and immunoglobulin levels in mammalian sera" *J. Immunol. Meth.* 62:1–13 (1983).

Linsley et al., "Binding of the B Cell Activation Antigen B7 to CD28 Costimulates T Cell Proliferation and Interleukin 2 mRNA Accumulation" *Journal of Experimental Medicine* 173:721–730 (1991).

Linsley et al., "CTLA–4 is a second receptor for the B cell activation antigen B7" *Journal of Experimental Medicine* 174:561–569 (1991).

Luckow et al., "Trends in the Development of Baculovirus Expression Vectors" *Bio/Technology* 6:47–55 (1988).

Lusky et al., "Bovin Papilloma Virus Contains an Activator of Gene Expression at the Distal End of the Early Transcription Unit" *Molecular & Cellular Biology* 3(6):1108–1122 (Jun. 1983).

Lutz–Freyermuth et al., "Quantitative Determination That One of Two Potential RNA–binding Domains of the A Protein Component of the U1 Small Nuclear Ribonucleoprotein Complex Binds with High Affinity to Stem–loop II of U1 RNA" *Proc. Natl. Acad. Sci. USA* 87:6393–6397 (1990).

Maeda et al., "Production of Human α–interferon in Silkworm Using a Baculovirus Vector" *Nature* 315:592–594 (Jun. 13, 1985).

Mansour et al., "Disruption of the Proto–oncogene int–2 in Mouse Embryo–derived Stem Cells: a General Strategy for Targeting Mutations to Non–selectable Genes" *Nature* 336:348–352 (1988).

Mantei et al., "Rabbit β–globin mRNA Production in Mouse L Cells Transformed with Cloned Rabbit β–globin Chromosomal DNA" *Nature* 281:40–46 (Sep. 6, 1979).

Marks et al., "By–passing immunization: building high affinity human antibodies by chain shuffling" *Bio/Technology* 10:779–783 (1992).

Marks et al., "By–passing immunization: human antibodies from V–gene libraries displayed on phage" *J. Mol. Biol.* 222:581–597 (1991).

Martin et al., "Efficient neutralization and disruption of rhinovirus by chimeric ICAM–1/immunoglobulin molecules" *Journal of Virology* 67:3561–3568 (1993).

Martin et al., "Gap Domains Responsible for Ras p21–Dependent Inhibition of Muscarinic Atrial $K^+$ Channel Currents" *Science* 255:192–194 (1992).

Mather et al., "Culture of Testicular Cells in Hormone–Supplemented Serum–Free Medium" *Annals N.Y. Acad. Sci.* 383:44–68 (1982).

Mather et al., "Establishment and Characterization of Two Distinct Mouse Testicular Epithelial Cell Lines" *Biol. Reprod.* 23:243–252 (1980).

Matthews et al., "A receptor tyrosine kinase specific to hematopoietic stem and progenitor cell–enriched populations" *Cell* 65:1143–1152 (1991).

Maxam et al., "Sequencing End–labeled DNA with Base–Specific Chemical Cleavages" *Methods in Enzymology* 65:499–560 (1980).

McCafferty et al., "Phage antibodies: filamentous phage displaying antibody variable domains" *Nature* 348:552–554 (1990).

McMahon and Bradley, "The Wnt–1 (int–1) proto–oncogene is required for development of a large region of the mouse brain" *Cell* 62:1073–1085 (1990).

McMahon et al., "The Midbrain–Hindbrain Phenotype of Wnt–1/Wnt–1 Mice Results from Stepwise Deletion of Engrailed–Expressing Cells by 9.5 Days Postcoitum" *Cell* 69:581–595 (1992).

McMahon, A., "The Wnt Family of Developmental Regulators" *Trends in Genetics* 8(7):236–242 (1992).

Messing et al., "A System for Shotgun DNA Sequencing" *Nucleic Acids Research* 9(2):309–321 (1981).

Miller et al., "An Insect Baculovirus Host–Vector System for High–Level Expression of Foreign Genes" *Genetic Engineering,* Setlow et al., Plenum Publishing vol. 8:277–298 (1986).

Milstein et al., "Hybrid Hybridomas and Their Use in Immunohistochemistry" *Nature* 305:537–540 (1983).

Morata and Lawrence, "The development of wingless, a homeotic mutation of Drosophila" *Dev. Biol.* 56:277–240 (1977).

Morrison et al., "Chimeric Human Antibody Molecules: Mouse Antigen–binding Domains with Human Constant Region Domains" *Proc. Natl. Acad. Sci. USA* 81:6851–6855 (Nov. 1984).

Morrison et al., "The purification and characterization of fetal liver hematopoietic stem cells" *Proc. Natl. Acad. Sci.* 92(22):10302–10306 (1995).

Muench et al., "Bone marrow transplantation with interleukin–1 plus kit–ligand ex vivo expanded bone marrow accelerates hematopoietic reconstruction in mice without the loss of stem cell lineage and proliferative potential" *Blood* 81:3463–3473 (1993).

Muller et al., "Development of hematopoietic stem cell activity in the mouse embryo" *Immunity* 1:291–301 (1994).

Muller–Sieburg and Deryugina, "The stromal cells' guide to the stem cell universe" *Stem Cells* 13(5):477–486 (1995).

Mulligan et al., "Expression of a Bacterial Gene in Mammalian Cells" *Science* 209:1422–1427 (Sep. 1980).

Munson et al., "Ligand: A Versatile Computerized Approach for Characterization of Ligand–Binding Systems" *Analytical Biochemistry* 107:220–239 (1980).

Nusse and Varmus, "Many tumors induced by the mouse mammary tumor virus contain a provirus integrated in the same region of the host genome" *Cell* 31:99–109 (1982).

Nusse and Varmus, "Wnt genes" *Cell* 69:1073–1087 (1992).

Nygren, H., "Conjugation of Horseradish Peroxidase to Fab Fragments with Different Homobifunctional and Heterobifunctional Cross–Linking Reagents" *The Journal of Histochemistry and Cytochemistry* 30(5):407–412 (1982).

Orlic, et al., "Purification and Characterization of Heterogeneous Pluripotent hematopoietic stem Cell Populations Expressing High Levels of c–kit Receptor" *Blood* 82(3):762–770 (Aug. 1, 1993).

Osborne et al., "Transcription Control Region Within the Protein–coding Portion of Adenovirus E1A Genes" *Molecular & Cellular Biology* 4(7):1293–1305 (Jul. 1984).

Paborsky et al., "Mammalian Cell Transient Expression of Tissue Factor for the Production of Antigen" *Protein Eng.* 3(6):547–553 (1990).

Pain et al., "Preparation of Protein A–Peroxidase Monoconjugate Using a Heterobifunctional Reagent, and its Use in Enzyme Immunoassays" *Journal of Immunological Methods* 40:219–230 (1981).

Papkoff and Schryver, "Secreted int–1 protein is associated with the cell surface" *Mole. Cell. Biol.* 10:2723–2730 (1990).

Parr and McMahon, "Dorsalizing signal Wnt–7a required for normal polarity of D–V and A–P axes of mouse limb" *Nature* 374:350–353 (1995).

Parr et al., "Mouse Wnt Genes Exhibit Discrete Domains of Expression in the Early Embryonic CNS and Limb Buds" *Development* 119:247–261 (1993).

Pavlakis et al., "Expression of Two Human Growth Hormone Genes in Monkey Cells Infected by Simian Virus 40 Recombinants" *Proc. Natl. Acad. Sci. USA* 78(12):7398–7402 (Dec. 1981).

Pear et al., "Production of high–titer helper–free retroviruses by transient transfection" *Proc. Natl. Acad. Sci.* 90:8392–8396 (1993).

Peifer et al., "A Model System for Cell Adhesion and Signal Transduction in Drosophila" *Development–Supplement* pp. 163–176 (1993).

Pennica et al., "Cardiotrophin–1. Biological Activities and Binding to the Leukemia Inhibitory Factor Receptor/gp130 Signaling Complex" *Journal of Biological Chemistry* 270(1):10915–10922 (1995).

Pennica et al., "Expression Cloning of Cardiotrophin 1, a Cytokine That Induces Cardiac Myocyte Hypertrophy" *Proceedings of the National Academy of Sciences, USA* 92:1142–1146 (Feb. 1995).

Peppel et al., "A Tumor Necrosis Factor (TNF) Receptor–IgG Heavy Chain Chimeric Protien as a Bivalent Antagonist of TNF Acitivity" *Journal of Experimental Medicine* 174:1483–1489 (1991).

Ploemacher et al., "An in vitro limiting–dilution assay of long–term repopulating hematopoietic stem cells in the mouse" *Blood* 74:2755–2763 (1989).

Pluckthun, A., "Mono– and bivalent antibody fragments produced in *Escherichia coli:* engineering, folding and antigen binding" *Immunol. Revs.* 130:151–188 (1992).

Presta et al., "Humanization of an Antibody Directed Against IgE" *J. Immunol.* 151(5):2623–2632 (Sep. 1, 1993).

Presta, L., "Antibody Engineering" *Curr. Op. Struct. Biol.* 2:593–596 (1992).

Rebel et al., "Amplification of Sca–1+ Lin– WGA+ cells in serum–free cultures containing steel factor, interleukin–6, and erythropoietin with maintenance of cells with long–term in vivo reconstituting potential" *Blood* 83:128–136 (1994).

Rebel et al., "The repopulation potential of fetal liver hematopoietic stem cells in mice exceeds that of their adult bone marrow counterparts" *Blood* 87:3500–3507 (1996).

Reyes et al, "Expression of Human β–interferon cDNA Under the Control of a Thymidine Kinase Promoter from Herpes Simplex Virus" *Nature* 297:598–601 (Jun. 17, 1982).

Ridgway et al., "Expression and Activity of IgE Receptor Alpha Chain–IgG Chimeric Molecules" *Journal of Cell Biology* 115:250a (Abstract No. 1448) (1991).

Riechmann et al., "Reshaping Human Antibodies for Therapy" *Nature* 332:323–327 (Mar. 24, 1988).

Rijsewijk et al., "The Drosophila homolog of the mouse mammary oncogene int–1 is identical to the segment polarity gene wingless" *Cell* 50:649–657 (1987).

Rodrigues et al., "Engineering a humanized bispecific F(ab')2 fragment for improved binding to T cells" *Int. J. Cancer* (Suppl.) 7:45–50 (1992).

Roelink and Nusse, "Expression of Two Members of the Wnt Family During Mouse Development– restricted Temporal and Spatial Patterns in the Developing Neural Tube" *Genes and Development* 5:381–388 (1991).

Sambrook et al. *Molecular Cloning: A Laboratory Manual*, New York:Cold Spring Harbor Laboratory Press pps. Chapters 10–12 (1989).

Schall et al., "Molecular Cloning and Expression of a Receptor for Human Tumor Necrosis Factor" *Cell* 61:361–370 (Apr. 20, 1990).

Seed B., "An LFA–3 cDNA encodes a phospholipid–linked membrane protein homologous to its receptor CD2" *Nature* 329:840–842 (1987).

Shalaby et al., "Development of Humanized Bispecific Antibodies Reactive with Cytotoxic Lymphocytes and Tumor Cells Overexpressing the HER2 Protooncogene" *Journal of Experimental Medicine* 175:217–225 (Jan. 1, 1992).

Shaw et al., "A General Method for the Transfer of Cloned Genes to Plant Cells" *Gene* 23:315–330 (1983).

Siebenlist et al., "*E. Coli* RNA Polymerase Interacts Homologously with Two Different Promoters" *Cell* 20:269–281 (Jun. 1980).

Sims et al., "A Humanized CD18 Antibody Can Block Function Without Cell Destruction" *The Journal of Immunology* 151(4):2296–2308 (Aug. 1993).

Skerra, A., "Bacterial expression of immunoglobulin fragments" *Curr. Opinion in Immunol.* 5:256–262 (1993).

Skinner et al., "Use of the Glu–Glu–Phe C–terminal Epitope for Rapid Purification of the Catalytic Domain of Normal and Mutant ras GTPase–activating Proteins" *Journal of Biological Chemistry* 266:14163–14166 (1991).

Sojar et al., "A Chemical Method for the Deglycosylation of Proteins" *Archives of Biochemistry & Biophysics* 259(1):52–57 (1987).

Sreekrishna et al., "High level expression of heterologous proteins in methylotrophic yeast *Pichia pastoris*" *J. Basic Microbiol.* 28:265–278 (1988).

Stamenkovic et al., "The B Lymphocyte Adhesion Molecule CD22 Interacts with Leukocyte Common Antigen CD45RO on T Cells and α2–6 Sialyltransferase, CD75, on B Cells" *Cell* 66:1133–1144 (Sep. 20, 1991).

Stark et al., "Epithelial transformation of metanephric mesenchyme in the developing kidney regulated by Wnt–4" *Nature* 372:679–683 (1994).

Stinchcomb et al., "Isolation and Characterisation of a Yeast Chromosomal Replicator" *Nature* 282:39–43 (Nov. 1, 1979).

Suresh et al., "Bispecific Monoclonal Antibodies from Hybrid Hybridomas" *Methods in Enzymology* 121:210–228 (1986).

Takada et al., "Wnt–3a regulates somite and tailbud formation in the mouse embryo" *Genes Dev.* 8:174–189 (1994).

Tam and Quinlan, "Mapping vertebrate embryos" *Curr. Biol.* 6:104–106 (1996).

Thomas and Cappechi, "Targeted disruption of the murine int–1 proto–oncogene resulting in severe abnormalities in midbrain and cerebellar development" *Nature* 346:847–850 (1990).

Thotakura et al., "Enzymatic Deglycosylation of Glycoproteins" *Meth. Enzymol.* 138:350–359 (1987).

Tilburn et al., "Transformation by integration in *Aspergillus nidulans*" *Gene* 26(2–3):205–221 (1983).

Traunecker et al., "Bispecific Single Chain Molecules (Janusins) Target Cytotoxic Lymphocytes on HIV Infected Cells" *EMBO Journal* 10(12):3655–3659 (1991).

Traunecker et al., "Highly Efficient Neutralization of HIV with Recombinant CD4–immunoglobulin Molecules" *Nature* 339:68–70 (1989).

Urlaub et al., "Isolation of Chinese Hamster Cell Mutants Deficient in Dihydrofolate Reductase Activity" *Proc. Natl. Acad. Sci. USA* 77(7):4216–4220 (Jul. 1980).

Van den Berg et al., "Kluyveromyces as a Host for Heterologous Gene Expression: Expression and Secretion of Prochymosin" *Bio/Technology* 8:135–139 (1990).

Van Den Berg et al., "A Role for Members of the Wnt Gene Family in Human Hematopoiesis" *Blood* 88(10 Su 1 Pt 1):141A (Nov. 15, 1996).

Van Leeuwen et al., "Biological Activity of Soluble Wingless Protein in Cultured Drosophila Imaginal Disc Cells" *Nature* 368:342–344 (1994).

Van Solingen et al., "Fusion of Yeast Spheroplasts" *J. Bact.* 130:946–947 (1977).

Vant Veer et al., "Molecular cloning and chromosomal assignment of the human homolog of int–1, a mouse gene implicated in mammary tumorigenesis" *Mole. Cell. Biol.* 4:2532–2534 (1984).

Verhoeyen et al., "Reshaping Human Antibodies: Grafting an Antilysozyme Activity" *Science* 239:1534–1536 (Mar. 25, 1988).

Visser et al., "The Expression of Cytokine Receptors by Purified Hemopoietic Stem Cells" *Stem Cells* 11(Suppl. 2):49–55 (Jul. 1993).

Wagner et al., "Transferrin–polycation conjugates as carriers for DNA uptake into cells" *Proc. Natl. Acad. Sci.* 87:3410–3414 (1990).

Waterhouse et al., "Combinatorial infection and in vivo recombination: a strategy for making large phage antibody repertoires" *Nucleic Acids Research* 21:2265–2266 (1993).

Watson et al., "A Homing Receptor–IgG Chimera as a Probe for Adhesive Ligands of Lymph Node High Endothelial Venules" *Journal of Cell Biology* 110:2221–2229 (1990).

Watson et al., "Neutrophil Influx into an Inflammatory Site Inhibited by a Soluble Homing Receptor–IgG Chimaera" *Nature* 349:164–167 (1991).

Williams et al., "Fibronectin and VLA–4 in haematopoietic stem cell–microenvironment interactions" *Nature* 352:438–441 (1991).

Williams, D.A., "Ex vivo expansion of hematopoietic stem and progenitor cells—robbing Peter to pay Paul?" *Blood* 81(12):3169–3172 (1993).

Wineman et al., "Maintenance of high levels of pluripotent hematopoietic stem cells in vitro: effect of stromal cells and c–kit" *Blood* 81:365–372 (1993).

Wu et al., "Receptor–mediated in vitro gene transformation by a soluble DNA carrier system" *Journal of Biological Chemistry* 262(10):4429–4432 (1987).

Yaniv, M., "Enhancing Elements for Activation of Eukaryotic Promoters" *Nature* 297(6):17–18 (May 1982).

Yelton et al., "Transformation of *Aspergillus nidulans* by using a trpC plasmid" *Proc. Natl. Acad. Sci.* 81:1470–1474 (1984).

Zakany and Duboule, "Correlation of Expression of Wnt–1 in Developing Limbs with Abnormalities in Growth and Skeletal Patterning" *Nature* 362:546–549 (1993).

Zamecnik et al., "Inhibition of replication and expression of human T–cell lymphotropic virus type III in cultured cells by exogenous synthetic oligonucleotides complementary to viral RNA" *Proc. Natl. Acad. Sci.* 83:4143–4146 (1986).

Zeigler et al., "Cellular and Molecular Characterization of the Role of the FLK–2/FLT–3 Receptor Tyrosine Kinase in Hematopoietic Stem Cells" *Blood* 84(8):2422–2430 (1994).

Zola, "Using Monoclonal Antibodies: Soluble Antigens" *Monoclonal Antibodies: A Manual of Techniques,* CRC Press, Chapter 6, pp. 147–158 (1987).

Zoller et al., "Oligonucleotide–directed Mutagenesis Using M13–derived Vectors: An Efficient and General Procedure for the Production of Point Mutations in Any Fragment of DNA" *Nucl. Acids Res.* 10(20):6487–6500 (1982).

Zon, L., "Developmental biology of hematopoiesis" *Blood* 86(8):2876–2891 (1995).

Zsebo et al., "Identification, purification, and biological characterization of hematopoietic stem cell factor from buffalo rat liver—conditioned medium" *Cell* 63:195–201 (1990).

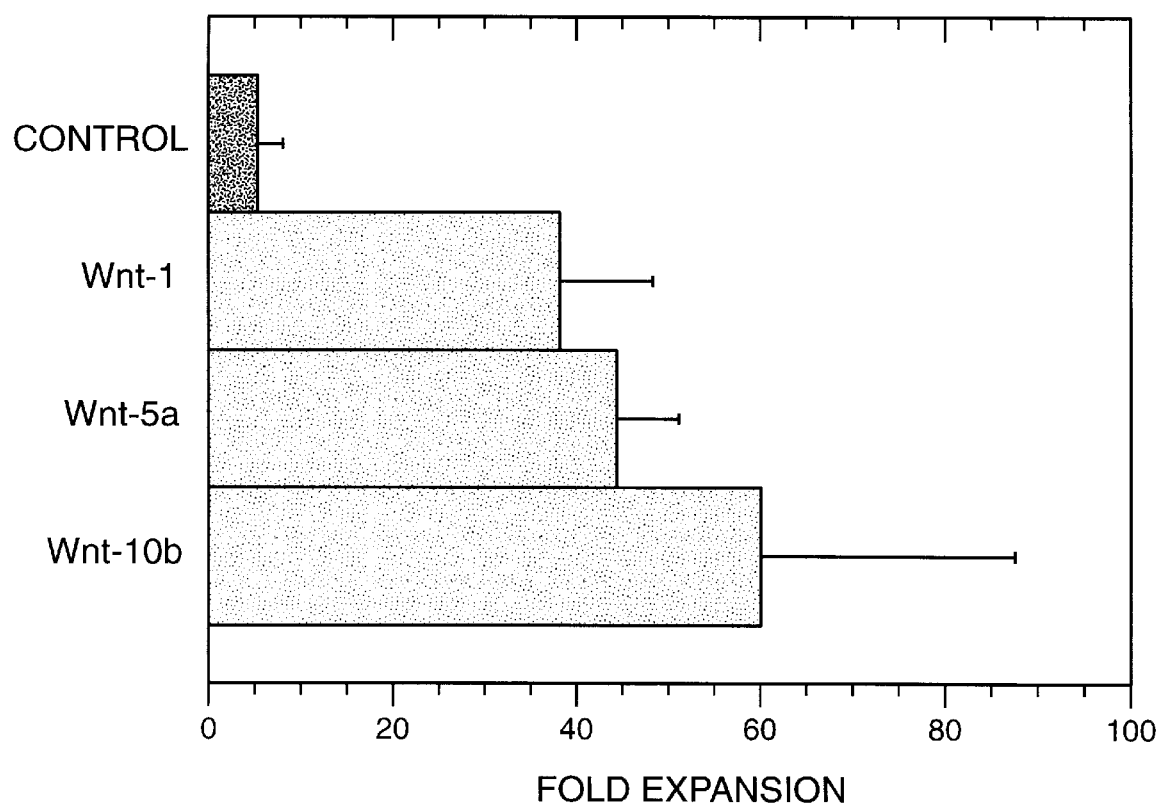
FIG._1

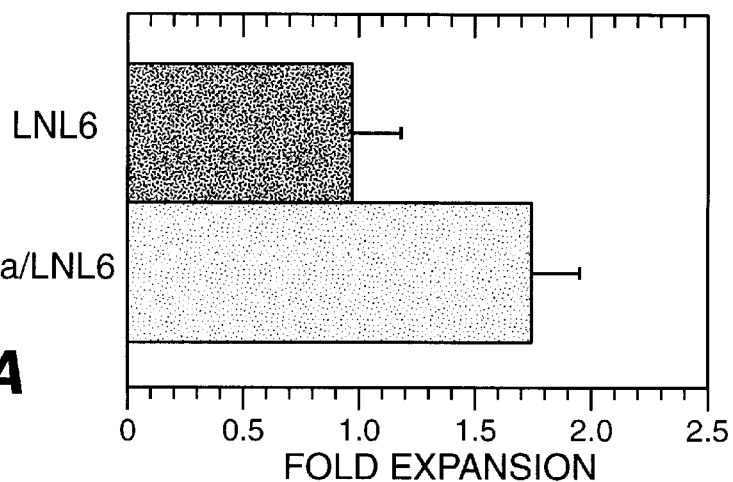
FIG._2A
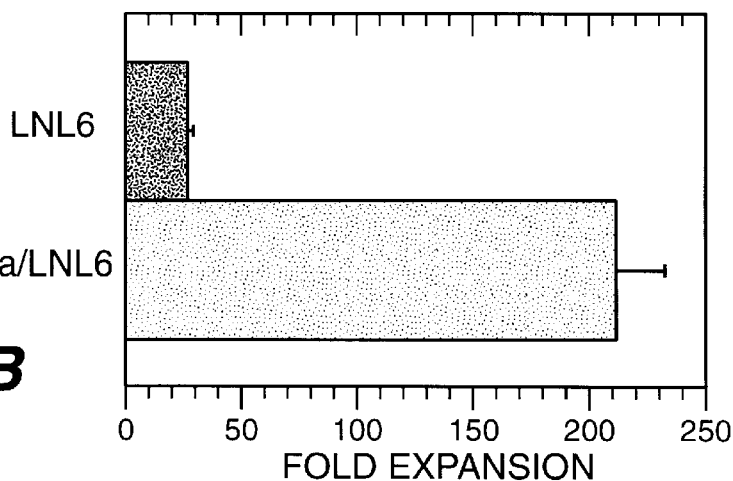
FIG._2B
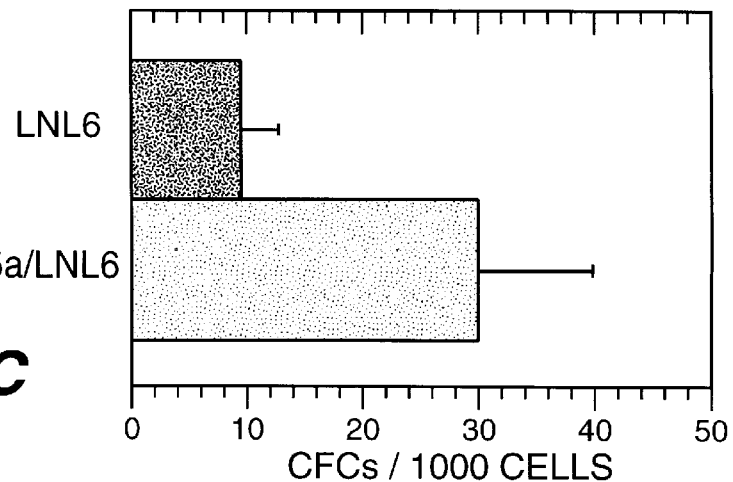
FIG._2C

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 10 amino acids
      (B) TYPE: Amino Acid
      (D) TOPOLOGY: Linear (xi) SEQUENCE DESCRIPTION: SEQ ID NO:1:

Asp Lys Thr His Thr Cys Pro Pro Cys Pro
1               5                   10

(2) INFORMATION FOR SEQ ID NO:2:

(i) SEQUENCE CHARACTERISTICS:
      (A) LENGTH: 36 base pairs
      (B) TYPE: Nucleic Acid
      (C) STRANDEDNESS: Single
      (D) TOPOLOGY: Linear (xi) SEQUENCE DESCRIPTION: SEQ ID NO:2:

CAAGAGTGCA AATGCCACGG GATGTCCGGC TCCTGC      36

(2) INFORMATION FOR SEQ ID NO:3:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:3:

CAAGAGTGCA AATGCCACGG GGTGTCCGGC TCCTGC                                         36

(2) INFORMATION FOR SEQ ID NO:4:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:4:

CTCAAGTGCA AATGCCACGG GCTATCTGGC AGCTGT                                         36

(2) INFORMATION FOR SEQ ID NO:5:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:5:

GTGGAGTGCA AGTGCCACGG GGTGTCCGGC TCCTGC                                         36

(2) INFORMATION FOR SEQ ID NO:6:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:6:

GTAGCCTGTA AGTGCCATGG AGTGTCTGGC TCCTGT                                         36

(2) INFORMATION FOR SEQ ID NO:7:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:7:

ACCGGGTGTA AGTGCCATGG GCTTTCGGGT TCCTGC                                         36

(2) INFORMATION FOR SEQ ID NO:8:

(i) SEQUENCE CHARACTERISTICS:
        (A) LENGTH: 36 base pairs
        (B) TYPE: Nucleic Acid
        (C) STRANDEDNESS: Single
        (D) TOPOLOGY: Linear (xi) SEQUENCE DESCRIPTION: SEQ ID NO:8:

CTGGAGTGTA AGTGCCATGG TGTGTCAGGC TCCTGT                                         36

(2) INFORMATION FOR SEQ ID NO:9:

(i) SEQUENCE CHARACTERISTICS:

(A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:9:

GCCSCGGCCR CARCACAT                                                 18

(2) INFORMATION FOR SEQ ID NO:10:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (xi) SEQUENCE DESCRIPTION: SEQ ID NO:10:

STGGARTGYA ARTGYCAT                                                 18

(2) INFORMATION FOR SEQ ID NO:11:

(i) SEQUENCE CHARACTERISTICS:
        (A) LENGTH: 15 base pairs
        (B) TYPE: Nucleic Acid
        (C) STRANDEDNESS: Single
        (D) TOPOLOGY: Linear (xi) SEQUENCE DESCRIPTION: SEQ ID NO:11:

RCARCACCAR TGRAA                                                    15

(2) INFORMATION FOR SEQ ID NO:12:

(i) SEQUENCE CHARACTERISTICS:
        (A) LENGTH: 12 base pairs
        (B) TYPE: Nucleic Acid
        (C) STRANDEDNESS: Single
        (D) TOPOLOGY: Linear (xi) SEQUENCE DESCRIPTION: SEQ ID NO:12:

GACCTGGTGT AC                                                       12

(2) INFORMATION FOR SEQ ID NO:13:

(i) SEQUENCE CHARACTERISTICS:
        (A) LENGTH: 15 base pairs
        (B) TYPE: Nucleic Acid
        (C) STRANDEDNESS: Single
        (D) TOPOLOGY: Linear (xi) SEQUENCE DESCRIPTION: SEQ ID NO:13:

TGYTGYGGCC GSGGC                                                    15

(2) INFORMATION FOR SEQ ID NO:14:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO:14:

CAGCCCAGGC GTCCGCGCTC                                               20

(2) INFORMATION FOR SEQ ID NO:15:

(i) SEQUENCE CHARACTERISTICS:
        (A) LENGTH: 20 base pairs (B) TYPE: Nucleic Acid
        (C) STRANDEDNESS: Single
        (D) TOPOLOGY: Linear (xi) SEQUENCE DESCRIPTION: SEQ ID NO:15:

GGAATGAACC CTGCTCCCGT                                                    20

(2) INFORMATION FOR SEQ ID NO:16:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:16:

CGCGCCCCAA GGACCTGCCT CG                                                 22

(2) INFORMATION FOR SEQ ID NO:17:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (xi) SEQUENCE DESCRIPTION: SEQ ID NO:17:

GCGAGCCAGT GCTCTCGTTG CG                                                 22

(2) INFORMATION FOR SEQ ID NO:18:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (xi) SEQUENCE DESCRIPTION: SEQ ID NO:18:

AAACCTGAAG CGGAAGTGCA AATGC                                              25

(2) INFORMATION FOR SEQ ID NO:19:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (xi) SEQUENCE DESCRIPTION: SEQ ID NO:19:

GCTCACCTTC ATTTACACAC ATTGA                                              25

(2) INFORMATION FOR SEQ ID NO:20:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (xi) SEQUENCE DESCRIPTION: SEQ ID NO:20:

GGAATTCCGG GCTTCGACAT GCTGGAGGA                                          29

(2) INFORMATION FOR SEQ ID NO:21:

(i) SEQUENCE CHARACTERISTICS:
        (A) LENGTH: 31 base pairs
        (B) TYPE: Nucleic Acid

```
        (C) STRANDEDNESS: Single
        (D) TOPOLOGY: Linear (xi) SEQUENCE DESCRIPTION: SEQ ID NO:21:

GGGGTACCCC AGGCTCACCT TCATTTACAC A                              31
```

USES OF WNT POLYPEPTIDES

CROSS REFERERENCE TO RELATED APPLICATIONS

This application claims priority under 35 U.S.C. § 119(e) of U.S. provisional application No. 60/024,068, having an effective filing date of Aug. 16, 1996.

FIELD OF THE INVENTION

This application relates to uses for Wnt polypeptides ("Wnts"). In particular, the invention relates to uses for a Wnt polypeptide for enhancing the proliferation, differentiation and/or maintenance of primitive hematopoietic cells, e.g., hematopoietic stem/progenitor cells.

BACKGROUND OF THE INVENTION

A. HEMATOPOIESIS

The process of blood cell formation whereby red and white blood cells are replaced through the division of cells located in the bone marrow is called hematopoiesis. For a review of hematopoiesis see Dexter and Spooncer (*Ann. Rev. Cell Biol.*, 3:423–441 [1987]).

There are many different types of blood cells which belong to distinct cell lineages. Along each lineage, there are cells at different stages of maturation. Mature blood cells are specialized for different functions. For example, erythrocytes are involved in $O_2$ and $CO_2$ transport; T and B lymphocytes are involved in cell and antibody mediated immune responses, respectively; platelets are required for blood clotting; and the granulocytes and macrophages act as general scavengers and accessory cells. Granulocytes can be further divided into basophils, eosinophils, neutrophils and mast cells.

Each of the various blood cell types arises from pluripotent or totipotent stem cells which are able to undergo self-renewal or give rise to progenitor cells or Colony Forming Units (CFU) that yield a more limited array of cell types. As stem cells progressively lose their ability to self-renew, they become increasingly lineage restricted. It has been shown that stem cells can develop into multipotent cells (called "CFC-Mix" by Dexter and Spooncer, supra). Some of the CFC-Mix cells can undergo renewal whereas others lead to lineage-restricted progenitors which eventually develop into mature myeloid cells (e.g., neutrophils, megakaryocytes, macrophages, basophils and erythroid cells). Similarly, pluripotent stem cells are able to give rise to PreB and PreT lymphoid cell lineages which differentiate into mature B and T lymphocytes, respectively. Progenitors are defined by their progeny, e.g., granulocytelmacrophagecolony-forming progenitor cells (GM-CFU) differentiate into neutrophils or macrophages; primitive erythroid burst-forming units (BFU-E) differentiate into erythroid colony-forming units (CFU-E) which give rise to mature erythrocytes. Similarly, the Meg-CFU, Eos-CFU and Bas-CFU progenitors are able to differentiate into megakaryocytes, eosinophils and basophils, respectively.

The number of pluripotent stem cells in the bone marrow is extremely low and has been estimated to be in the order of about one per 10,000 to one per 100,000 cells (Boggs et al., *J. Clin. Inv.*, 70:242 [1982] and Harrison et al., *PNAS*, 85; 822 [1988]). Accordingly, characterization of stem cells has been difficult. Therefore, various protocols for enriching pluripotent stem cells have been developed. See, for example, Matthews et al., *Cell*, 65:1143–1152 [1991]; WO 94/02157; Orlic et al., *Blood*, 82(3 :762–770 [1993]; and Visseret al., *Stem Cells*, 11Suppl. (2):49–55 [July 1993].

Various lineage-specific factors have been demonstrated to control cell growth, differentiation and the functioning of hematopoietic cells. These factors or cytokines include the interleukins (e.g., IL-3), granulocyte-macrophagecolony-stimulatingfactor (GM-CSF), macrophage colony-stimulating factor (M-CSF), granulocyte colony-stimulating factor (M-CSF), erythropoietin (Epo), lymphotoxin, steel factor (SLF), tumor necrosis factor (TNF) and gamma-interferon. These growth factors have a broad spectrum of activity, from generalized to lineage-specific roles in hematopoiesis, or a combination of both. For example, IL-3 appears to act on multipotent stem cells as well as progenitors restricted to the granulocytelmacrcphage, eosinophil, megakaryocyte, erythroid or mast cell lineages. On the other hand, Epo generally acts on fairly mature erythroid progenitor cells.

B. THE HEMATOPOIETIC ENVIRONMENT AND EMBRYOGENESIS

The capacity of the hematopoietic stem cells to provide for the lifelong production of all blood lineages is accomplished by a balance between the plasticity of the stem cell, that is the production of committed progenitors cells which generate specific blood lineages, and the replication of the stem cell in the undifferentiated state (self-renewal). The mechanisms regulating hematopoietic stem cells' plasticity and self-renewal in vivo have been difficult to define. However, the major contributory factors represent a combination of cell intrinsic and environmental influences (Morrison et al., *Proc. Natl. Acad. Sci. USA*, 92: 10302–10306 [1995]). The importance of the hematopoieticmicroenvironmenthas been established through the use of long term bone marrow culture systems where hematopoieticcells cultured on stroma allow for the maintenance of HSCs, albeit at low frequencies (Fraser et al., *Proc. Natl. Acad. Sci. USA*, 89: 1968–1972, [1992]; Wineman et al., *Blood*, 81: 365–372 [1993]).

The demonstration of hematopoietic cell maintenance in culture has led to efforts to identify candidate 'stem cell' factors. The role of hematopoietic cytokines in stem cell maintenance has been studied by direct addition of purified factors to in vitro cultures of stem cell populations followed by transplantation of the cultured cells (Muench et al., *Blood*, 81: 3463–3473 [1993]; Wineman et al., supra [1993]; Rebel et al., *Blood*, 83: 128–136 [1994]). Most of the known 'early-acting' cytokines such as IL-3, IL-6, and KL have been shown to stimulate proliferation of more committed progenitor cells while concurrently allowing maintenance, but not expansion, of cells capable of long-term multilineage repopulation (reviewed in Williams, *Blood*, 81(12) :3169–3172 [1993]; Müller-Sieburg and Deryugina, *Stem Cells*, 13: 477–486 [1995]). While these data indicate that the cells' plasticity and repopulating function may be preserved by cytokine treatment, the molecules that promote self-renewal of these pluripotent cells remain unknown.

Transplantation studies have shown that the signals that regulate fate pluripotent stem cells may be similar in the embryo and adult bone marrow. Cells from the day 11 fetal liver, yolk sac, or aorta/gonad/mesonephros (AGM) region can repopulate the adult marrow and appropriately respond to extrinsic cues to sustain long-term multilineage hematopoiesis (Müller et al., *Immunity*, 1:291–301 [1994]). Although embryonic hematopoiesis is largely devoted to the erythroid lineage, the embryonic microenvironment clearly contributes to the maintenance of pluripotent stem cells in the undifferentiatedstate. These cell populations are cycling during embryogenesis (Zeigler et al., supra [1994]; Morrison et al., supra [1995]; Rebel et al., *Blood*, 87: 3500–3507 [1996]).

In mammals, hematopoietic precursors arise in the extraembryonic and ventral mesoderm, yolk sac, or AGM region (Dzierzak and Medvinsky *Trends Genet.,* 11: 359–366 [1995]; Zon, *Blood,* 86: 2876–2891 [1995]). In amphibian embryos, the equivalent regions are the ventral blood island mesoderm and the dorsal lateral plate mesoderm (reviewed in Kessler and Melton, *Science,* 266: 596–604 [1994]; Zon, supra 1995; Tam and Quinlan, *Curr. Biol.,* 6: 104–106 [1996]). Secreted factors that potentially regulate cell fate determination of ventral mesoderm in Xenopus include Wnts, FGFs, and BMP-4 (reviewed in Christian and Moon, *Bio Essays,* 15: 135–140 [1993a]; Zon, supra [1995]). Embryonic expression of XWnt-8 (Christian and Moon, *Genes Dev.,* 7: 13–28 [1993b]) and XWnt-11(Ku and Melton, *Development,* 119: 1161–1173 1993]) is localized to the area of prospective ventral and lateral mesoderm and XWnt-8 expression can be induced by ventralizing factors such as FGFs and BMP-4.

C. THE WNTS GENE FAMILY

Wnts are encoded by a large gene family whose members have been found in round worms, insects, cartilaginous fish and vertebrates (Sidow, 1994). Wnts are thought to function in a variety of developmental and physiological processes since many diverse species have multiple conserved Wnt genes (McMahon, *Trends Genet.,* 8: 236–242 [1992]; Nusse and Varmus, *Cell,* 69: 1073–1087 [1992]). Wnt genes encode secreted glycoproteins that are thought to function as paracrine or autocrine signals active in several primitive cell types (McMahon, supra [1 992]; Nusse and Varmus, supra [1992]). The Wnt growth factor family includes more than 10 genes identified in the mouse (Wnt-1, 2, 3a, 3b, 4, 5a, 5b, 6, 7a 7b, 8a, 8b, 10b, 11, 12) (see, e.g., Gavin et al., *Genes Dev.,* 4: 2319–2332 [1990]; Lee et al., *Proc. Natl. Acad. Sci. USA,* 92: 2268–2272; Christiansen et al., *Mech. Dev.* 51: 341–350 [1995]) and at least 7 genes identified in the human (Wnt-1, 2, 3,4, 5a, 7a and 7b) by cDNA cloning (see, e.g., Vant Veer et al., *Mol. Cell. Biol.,* 4: 2532–2534 [1984]). The Wnt-1 proto-oncogene (int-1) was originally identified from mammary tumors induced by mouse mammary tumor virus (MMTV) due to an insertion of viral DNA sequence (Nusse and Varmus, *Cell,* 31: 99–109 [1982]). In adult mice, the expression level of Wnt-1 mRNA is detected only in the testis during later stages of sperm development. Wnt-1 protein is about 42 KDa and contains an amino terminal hydrophobic region, which may function as a signal sequence for secretion (Nusse and Varmus, supra). The expression of Wnt-2/irp is detected in mouse fetal and adult tissues and its distribution does not overlap with the expression pattern for Wnt-1. Wnt-3 is associated with mouse mammary tumorigenesis. The expression of Wnt-3 in mouse embryos detected in the neural tubes and in the limb buds. Wnt-5a transcripts are detected in the developing fore- and hind limbs at 9.5 through 14.5 days and highest levels are concentrated in apical ectoderm at the distal tip of limbs (Nusse and Varmus, supra [1992]. Recently, a Wnt growth factor, termed Wnt-x, was described (PCT/US94/14708; W095/17416) along with the detection of Wnt-x expression in bone tissues and in bone-derived cells. Also described was the role of Wnt-x in the maintenance of mature osteoblasts and the use of the Wnt-x growth factor as a therapeutic agent or in the development of other therapeutic agents to treat bone-related diseases.

Wnts may play a role in local cell signaling. Biochemical studies have shown that much of the secreted Wnt protein can be found associated with the cell surface or extracellular matrix rather than freely diffusible in the medium (Papkoff and Schryver, *Mol. Cell. Biol.,* 10: 2723–2730 [1990]; Bradley and Brown, *EMBO J.,* 9: 1569–1575 [1990]).

Studies of mutations in Wnt genes have indicated a role for Wnts in growth control and tissue patterning. In Drosophila, wingless (wg) encodes a Wnt gene (Rijsenijk et al., *Cell.* 50: 649–657 [1987]) and wg mutations alter the pattern of embryonic ectoderm, neurogenesis, and imaginal disc outgrowth (Morata and Lawrence, *Dev. Biol.,* 56: 227–240 [1977]; Baker, *Dev. Biol.,* 125: 96–108 [1988]; Klingensmith and Nusse, *Dev. Biol.,* 166: 396–414[1994]). In Caenorhabditis elegans, lin-44 encodes a Wnt which is required for asymmetric cell divisions (Herman and Horvitz, *Development,* 120: 1035–1047 [1994]). Knock-out mutations in mice have shown Wnts to be essential for brain development (McMahon and Bradley, *Cell,* 62: 1073–1085 [1990]; Thomas and Cappechi, *Nature,* 346: 847–850 [1990]), and the outgrowth of embryonic primordia for kidney (Stark et al., *Nature,* 372: 679–683 [1994]), tail bud (Takada et al., *Genes Dev.,* 8: 174–189 [1994]), and limb bud (Parr and McMahon, *Nature,* 374: 350–353 [1995]). Overexpression of Wnts in the mammary gland can result in mammary hyperplasia (McMahon, supra (1992]; Nusse and Varmus, supra [1992]), and precocious alveolar development (Bradbury et al., *Dev. Biol.,* 170: 553–563 [1995]). A role for Wnts in mammalian hematopoiesis has not previously been suggested or considered.

Wnt-5a and Wnt-5b are expressed in the posterior and lateral mesoderm and the extraembryonic mesoderm of the day 7–8 murine embryo (Gavin et al., supra [1990]). These embryonic domains contribute to the AGM region and yolk sac tissues from which multipotent hematopoietic precursors and HSCs are derived (Dzierzak and Medvinsky, supra [1995]; Zon, supra [1995], Kanatsu and Nishikawa, *Development,* 122: 823–830 [1996]). Wnt-5a, Wnt-10b, and other Wnts have been detected in limb buds, indicating possible roles in the development and patterning of the early bone microenvironment as shown for Wnt-7b (Gavin et al., supra [1990]; Christiansen et al., *Mech. Devel.,* 51: 341–350 [1995]; Parr and McMahon, supra [1995]).

D. HEMATOPOIETIC DISEASES AND DISORDERS

Chemo- and radiation therapies cause dramatic reductions in blood cell populations in cancer patients. At least 500,000 cancer patients undergo chemotherapy and radiation therapy in the US and Europe each year and another 200,000 in Japan. Bone marrow transplantation therapy of value in aplastic anemia, primary immunodeficiency and acute leukemia (following total body irradiation) is becoming more widely practiced by the medical community. At least 15,000 Americans have bone marrow transplants each year. Other diseases can cause a reduction in entire or selected blood cell lineages. Examples of these conditions include anemia (including macrocytic and aplastic anemia); thrombocytopenia; hypoplasia; immune (autoimmune) thrombocytopenic purpura (ITP); and HIV induced ITP.

Pharmaceutical products are needed which are able to enhance reconstitution of blood cell populations of these patients.

Accordingly, it is an object of the present invention to provide a method for enhancing the proliferation and/or differentiation and/or maintenance of primitive hematopoietic cells. Such a method may be useful for enhancing repopulation of hematopoietic stem cells and thus mature blood cell lineages. This is desirable where a mammal has suffered a decrease in hematopoietic or mature blood cells as a consequence of disease, radiation or chemotherapy. This method is also useful for generating expanded populations of such stem cells and mature blood cell lineages from such hematopoietic cells ex vivo.

These and other objects will be apparent to the ordinary artisan upon consideration of the specification as a whole.

SUMMARY OF THE INVENTION

In one aspect, the present invention pertains to the discovery herein that Wnt polypeptides ("Wnts"), such as Wnt-5a, play a role in hematopoiesis. In another aspect, the present invention is based on the observation that such Wnts function as hematopoietic regulatory factors and are able to directly stimulate the proliferation of hematopoietic stem cells, trigger the formation of multicellular aggregates or 'foci' of primitive blast cells, and expand the total number of multipotential colony forming cells via receptor signalling. Wnts appeared to directly act at the level of the early hematopoietic precursor (i.e., hematopoieticstem/progenitorcells). Such an expanded stem cell population can serve as the source of cells for myelopoiesis, erythropoiesis (e.g., splenic erythropoiesis) and lymphopoiesis. Accordingly, Wnts can be used to stimulate proliferation and/or differentiation and/or maintenance of hematopoietic stem/progenitor cells either in vitro or in vivo (e.g., for treating hematopoietic diseases or disorders).

Thus, the invention provides a method for enhancing proliferation, differentiation and/or maintenance of a cell with a Wnt polypeptide comprising the step of contacting the cell with an amount of Wnt polypeptide which is effective for stimulating proliferation and/or differentiation and/or maintenance (e.g., survival) of the cell. In preferred embodiments, the cell which is exposed to the Wnt polypeptide is a hematopoietic precursor, e.g., a hematopoietic stem/progenitor cell. For example, the Wnt polypeptide may be Wnt-1, Wnt-5a or Wnt-10b. For in vivo use, the Wnt polypeptide of choice may be a long half-life derivative of, for example, a Wnt-5a polypeptide such as Wnt-5a immunoglobulin chimera and/or Wnt-5a polypeptide modified with a nonproteinaceous polymer, such as polyethylene glycol (PEG). The method contemplated herein may lead to an increase in the proliferation and/or differentiation of lymphoid, myeloid and/or erythroid blood cell lineages from the maintained or expanded hematopoietic stem/progenitor cell population and encompasses both in vitro and in vivo methods. For in vitro uses, the cell stimulated by Wnts may be present in cell culture. As to in vivo methods, the cell may be present in a mammal, especially a human (e.g., one who is suffering from decreased blood levels and who could benefit from an increase in various blood cells). Potential patients include those who have undergone chemo- or radiation therapy, or bone marrow transplantation therapy. Thus, the invention provides a method for repopulating blood cells (e.g., erythroid, myeloid and/or lymphoid blood cells) in a mammal comprising administering to the mammal a therapeutically effective amount of Wnt polypeptide.

Mammals which may benefit from an enhancement of lymphopoiesis include those predisposed to, or suffering from, any one or more of the following exemplary conditions: lymphocytopenia; lymphorrhea; lymphostasis; immunodeficiency (e.g., HIV and AIDS); infections (including, for example, opportunistic infections and tuberculosis (TB)); lupus; and other disorders characterized by lymphocyte deficiency. An effective amount of the Wnt polypeptide can be used in a method of immunopotentiation or to improve immune function in a mammal.

Diseases or disorders in which an increase in erythropoiesis may be beneficial include, but are not limited to: erythrocytopenia; erthrodegenerative disorders; erythroblastopenia; leukoerythroblastosis; erythroclasis; thalassemia; and anemia (e.g., hemolytic anemia, such as acquired, autoimmune, or microangiopathichemolytic anemia; aplastic anemia; congenital anemia, e.g., congenital dyserythropoietic anemia, congenital hemolytic anemia or congenital hypoplastic anemia; dyshemopoietic anemia; Faconi's anemia; genetic anemia; hemorrhagic anemia; hyperchromic or hypochromic anemia; nutritional, hypoferric, or iron deficiency anemia; hypoplastic anemia; infectious anemia; lead anemia; local anemia; macrocytic or microcytic anemia; malignant or pernicious anemia; megaloblastic anemia; molecular anemia; normocytic anemia; physiologic anemia; traumatic or posthemorrhagic anemia; refractory anemia; radiation anemia; sickle cell anemia; splenic anemia; and toxic anemia).

An increase in myelopoiesis may be beneficial in any of the above-mentioned diseases or disorders as well as the following exemplary conditions; myelofibrosis; thrombocytopenia; hypoplasia; disseminated intravascularcoagulation (DIC); immune (autoimmune)thrombocytopenio purpura (ITP); HIV inducted ITP; myelodysplasia; thrombocytotic diseases and thrombocytosis.

The method may further involve the step of exposing hematopoieti cells (whether they be in cell culture or in a mammal) to one or more other cytokines (e.g., lineage-specificcytokines) and this may lead to a synergistic enhancement of the proliferation and/or differentiation of the cells. Exemplary cytokines include thrombopoietin (TPO); erythropoietin (EPO); macrophage-colony stimulating factor (M-CSF); granulocyte-macrophage CSF (GM-CSF); granulocyte-CSF (G-CSF); interleukin-1 (IL-1); IL-1a; IL-2, IL-3, IL-4, IL-5, IL-6, IL-7, IL-8, IL-9; IL-11; IL10; IL-12; leukemia inhibitoryfactor (LIF) or kit ligand (KL). In this embodiment, exposure to the cytokine may proceed, occur simultaneously with, or follow, exposure to the Wnt polypeptide. Preferably, the Wnt polypeptide and one or more further cytokines are administered simultaneously to the patient (where the method is an in vivo one) and, optionally, are combined to form a pharmaceutical composition.

For use in the above methods, the invention also provides an article of manufacture, comprising: a container, a label on the container, and a composition comprising an active agent within the container, wherein the composition is effective for enhancing proliferation and/or differentiation and/or maintenance of hematopoietic stem/progenitor cells in a mammal, the label on the container indicates that the composition can be used for enhancing proliferation and/or differentiation and/or maintenance of those cells and the active agent in the composition is a Wnt polypeptide. Optionally, the article of manufacture includes one or more further containers which hold further cytokine(s) in a packaged combination with the container holding the Wnt polypeptide.

In another embodiment, an effective amount of the Wnt polypeptide may be used to improve engraftment in bone marrow transplantation or to stimulate mobilization and/or expansion of hematopoietic stem cells in a mammal prior to harvesting hematopoietic progenitors from the peripheral blood thereof.

In addition to the above, the invention provides isolated nucleic acid molecules, expression vectors and host cells encoding a Wnt polypeptide which can be used in the recombinant production of Wnts as described herein. The isolated nucleic acid molecules and vectors are also useful for gene therapy applications to treat patients, for example, to increase the number of cells expressing a Wnt polypeptide and increase Wnt responsiveness. In addition, anti-Wnt antibodies, in particular, neutralizing antibodies to Wnts, are useful for the treatment of disorders, stem cell tumors and other tumors at sites of Wnt expression, including those tumors characterized by overexpression of Wnts.

BRIEF DESCRIPTION OF THE DRAWINGS

FIG. 1 is a graph showing Wnts promotion of cell proliferation in suspension cultures of flASK cells. The fold expansions in cell number following culture for 7 days are shown. Cultures were initiated with flASK cells (5000/well), 25 ng/ml KL, and conditioned media (CM) from 293 cells transfected with control plasmid, Wnt-1, Wnt-5a (gDWnt5aHis$_6$), or Wnt-10b. Assays were performed in duplicate and repeated in two independent experiments.

FIG. 2A, B and C are graphs showing Wnts promotion of enhanced fold expansion and colony formation from flASK cells. FIG. 2A shows enhanced survival/proliferation of flASK cells following transduction with the Wnt5a/LNL6 retrovirus. Transductions were initiated with 100,000 cells/ml in IL-3, IL-6, and KL. The fold expansion for LNL6 or Wnt5a/LNL6-treated cells was determined from cell counts at the end of the transduction period (48 hours) and repeated four times. FIG. 2B shows that suspension culture of Wnt5a/LNL6 transduced cells for 7 days results in extensive expansion compared to LNL6-treated cultures. FIG. 2C shows the colony formation from flASK cells following a 48 hour transduction with LNL6 or Wnt5a/LNL6. Cells were plated in quadruplicate in myeloid methylcellulose, colony growth was evaluated after day 12 of culture, and repeated in four independent experiments.

DETAILED DESCRIPTION OF THE PREFERRED EMBODIMENTS

A search to uncover novel self-renewal factors from investigations on the embryonic and fetal hematopoietic microenvironment has led to the discovery that Wnt polypeptides comprise a novel class of stem cell regulators and directly stimulate the extensive proliferation and/or differentiation and/or maintenance of cultured hematopoietic stem/progenitor cells. Wnt polypeptides are thus useful in vivo or ex vivo to enhance proliferation and/or differentiation and/or maintenance of hematopoietic stem/progenitor cells, expand the population of these cells and enhance repopulation of such cells and blood cells of multiple lineages in a mammal.

I. Definitions

In describing the present invention, the following terms will be employed, and are intended to be defined as indicated below.

The terms "Wnts" or "Wnt gene product" or "Wnt polypeptide" when used herein encompass native sequence Wnt polypeptides, Wnt polypeptide variants, Wnt polypeptide fragments and chimeric Wnt polypeptides. Optionally, the Wnt polypeptide is not associated with native glycosylation. "Native glycosylation" refers to the carbohydrate moieties which are covalently attached to Wnt polypeptide-when it is produced in the mammalian cell from which it is derived in nature. Accordindy, a human Wnt polypeptide produced in a non-human cell is an example of a Wnts which is "not associated with native glycosylation". Sometimes, the Wnt polypeptide is unglycosylated (e.g., as a result of being produced recombinantly in a prokaryote).

A "native sequence" polypeptide is one which has the same amino acid sequence as a polypeptide (e.g., Wnt polypeptide) derived from nature. Such native sequence polypeptides can be isolated from nature or can be produced by recombinant or synthetic means. Thus, a native sequence polypeptidecan have the amino acid sequence of naturally-occurring human polypeptide, murine polypeptide, or polypeptide from any other mammalian species.

The term "native sequence Wnt polypeptide" includes those Wnt polypeptides from any animal species (e.g., human, murine, rabbit, cat, cow, sheep, chicken, procine, equine, etc.) as occurring in nature. The definition specifically includes human Wnt polypeptides, Wnt-1, 2, 3, 4, 5a, 7a and 7b and murine Wnt polypeptides, Wnt-1, 2, 3a, 3b, 4, 5a, 5b, 6, 7a, 7b, 8a, 8b, 10b, 11 and 12. The term "native sequence Wnt protein" includes the native proteins with or without the initiating N-terminal methionine (Met), and with or without the native signal sequence. The native sequence human and murine Wnt polypeptides known in the art are from about 348 to about 389 amino acids long in their unprocessed form reflecting variability (particularly at the poorly conserved amino-terminus and several internal sites), contain 21 conserved cysteines, and have the features of a secreted protein (see, e.g., Wnt polypeptides as in Gavin et al., supra; Lee et al., supra; Christiansen et al., supra; PCT/US94/14708 [WO 95/17416]). The molecular weight of a Wnt polypeptide is about 38–42 kD in a monomeric form.

A "variant" polypeptide means a biologicallyactive polypeptideas defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active Wnt variant will have an amino acid sequence having at least about 90% amino acid sequence identity with a native sequence Wnt polypeptide, preferably at least about 95%, more preferably at least about 99%.

A "chimeric"Wnt polypeptide is a polypeptide comprising a Wnt polypeptide or portion (e.g., one or more domains) thereof fused or bonded to heterologous polypeptide. The chimeric Wnt polypeptide will generally share at least one biological property in common with a native sequence Wnt polypeptide, such as Wnt-5a. Examples of chimeric polypeptides include immunoadhesins and epitope tagged polypeptides.

The term "Wnt immunoadhesin" is used interchangeably with the expression "Wnt polypeptide-immunoglobulin chimera" and refers to a chimeric molecule that combines a portion of the Wnt polypeptide with an immunoglobulin sequence. The immunoglobulin sequence preferably, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but preferably IgG1 or IgG3.

The term "epitope tagged" when used herein refers to a chimeric polypeptide comprising a Wnt polypeptide or portion thereof fused to a "tag polypeptide". The tag polypeptide has enough residues to provide an epitope against which an antibody thereagainst can be made, yet is short enough such that it does not interfere with biological activity of the Wnt polypeptide. The tag polypeptide preferably also is fairly unique so that the antibody thereagainst does not substantially cross-react with other epitopes. Suitable tag polypeptides generally have at least six amino acid residues and usually between about 6–60 amino acid residues.

"Isolated" Wnt polypeptide means has been purified from a Wnts source or has been prepared by recombinant or synthetic methods and is sufficiently free of other peptides or proteins (1) to obtain at least 15 and preferably 20 amino acid residues of the N-terminal or of an internal amino acid sequence by using a spinning cup sequenatoror the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less than about 5% contamination with other source proteins.

"Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

"Biological property" when used in conjunction with either "Wnt polypeptide" or "isolated Wnt polypeptide" means having an effectorfunction that is directly or indirectly caused or performed by native sequence Wnt polypeptide, such as Wnt-5a. Effector functions of native sequence Wnt polypeptides include enhancement of differentiation and/or proliferation and/or maintenance of hematopoietic/progenitorcells (e.g., as determined in assays described in Examples 1 and 2). A "biologically active Wnt polypeptide" is one which possesses a biological property of native sequence Wnt polypeptide.

A "functional derivative" of a native sequence Wnt polypeptide is a compound having a qualitative biological property in common with a native sequence Wnt polypeptide. "Functional derivatives" include, but are not limited to, fragments of a native sequence and derivatives of a native sequence Wnt polypeptide and its fragments, provided that they have a biological activity in common with a corresponding native sequence Wnt polypeptide. The term "derivative" encompasses both amino acid sequence variants of Wnt polypeptide and covalent modifications thereof.

The phrase "long half-life" as used in connection with Wnt polypeptides, concerns Wnt derivatives having a longer plasma half-life and/or slower clearance than a corresponding native sequence Wnt polypeptide. The long half-life derivatives preferably will have a half-life at least about 1.5-times longer than a native Wnt polypeptide; more preferably at least about 2-times longer than a native Wnt polypeptide, more preferably at least about 3-times longer than a native Wnt polypeptide.

"Percent amino acid sequence identity" is defined herein as the percentage of amino acid residues in the candidate sequence that are identical with the residues in the native sequence, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the candidate sequence shall be construed as affecting sequence identity or homology.

The expression "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accordance with conventional practice.

As used herein, the expressions "cell," "cell line," and "cell culture" are used interchangeablyand all such designationsinclude progeny. Thus, the words "transformants" and "transformed cells" or "transfectants" and "transfected cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The term "antibody" is used in the broadest sense and specifically covers monoclonal antibodies, antibody compositionswith polyepitopic specificity, bispecific antibodies, diabodies, and single-chain molecules, as well as antibody fragments (e.g., Fab, F(ab')$_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohleret al., Nature 256:495 [1975], or may be made by recombinant DNA methods (see, e.g., U.S. Pat. No. 4,816,567 (Cabilly et al.)). The "monoclonal antibodies" may also be isolated from phage antibody libraries using the techniques in Clackson et al., Nature 352:624–628 [1991] and Marks et al., J. Mol. Biol. 222:581–597 [1991], for example.

The monoclonal antibodies herein specifically include "chimeric" antibodies (immunoglobulins) in which a portion of the heavy and/or light chain is identical with or homologous to corresponding sequences in antibodies derived from a particular species or belonging with or homologous to corresponding sequences in antibodies derived from another species or belonging to another antibody class or subclass, as well as fragments of such antibodies, so long as they exhibitthe desired biological activity (Cabilly et al., supra; Morrison et al., *Proc. Natl. Acad. Sci. USA*, 81:6851–6855 [1984]).

"Humanized" forms of non-human (e.g., murine) antibodies are chimeric immunoglobulins, immunoglobulin chains or fragments thereof (such as Fv, Fab, Fab, F(ab)$_2$ or otherantigen-bindirg subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin sequence. The humanized antibody optimally also will comprise at least a portion of an immunoglobulin constant region (Fc), typically that of a human immunoglobulin. For further details, see Jones et al., *Nature* 321:522–525[*1986*]; Riechmann et al., *Nature* 332:323–327 [1988]; and Presta, *Curr. Op. Struct. Biol* 2:593–596 [1992]. The humanized antibody includes a Primatized® antibody wherein the antigen-binding region of the antibody is derived from an antibody produced by immunizing macaque monkeys with the antigen of interest.

"Non-immunogenicin a human" means that upon contacting the polypeptide of interest in a physiologically acceptable carrier and in a therapeutically effective amount with the appropriate tissue of a human, no state of sensitivityor resistanceto the polypeptide of interest is demonstrated upon the second administration of the polypeptide of interest after an appropriate latent period (e.g., 8 to 14 days).

The phrase "enhancing proliferation of a cell" encompasses the step of increasing the extent of growth and/or reproduction of the cell relative to an untreated cell either in vitro or in vivo. An increase in cell proliferation in cell culture can be detected by counting the number of cells before and after exposure to a molecule of interest. The extent of proliferation can be quantified via microscopicexamination of the degree of confluency. Cell proliferation can also be quantified using a thymidine incorporation assay.

By "enhancing differentiation of a cell" is meant the act of increasing the extent of the acquisition or possession of one or more characteristics or functions which differ from that of the original cell (i.e., cell specialization). This can be detected by screening for a change in the phenotype of the cell (e.g., identifying morphological changes in the cell and/or surface markers on the cell).

By "enhancing survival or maintenance of a cell" encompasses the step of increasing the extent of the possession of one or more characteristics or functions which are the same as that of the original cell (i.e., cell phenotype maintenance). This can be detected by screening for the maintenance of the cell's phenotype (e.g., blast cell phenotype as in Example 2).

A "hematopoieticstem/progenitorcell" or "primitive hematopoieticcell" is one which is able to differentiate to form a more committed or mature blood cell type.

A "hematopoieticstem cell" or "stem cell" is one which is specifically capable of long-term engraftment of a lethally irradiated host.

"Lymphoid blood cell lineages" are those hematopoietic precursor cells which are able to differentiate to form lymphocytes (B-cells or T-cells). Likewise, "lymphopoeisis" is the formation of lymphocytes.

"Erythroid blood cell lineages" are those hematopoietic precursor cells which are able to differentiate to form erythrocytes (red blood cells) and "erythropoeisis" is the formation of erythrocytes.

The phrase "myeloid blood cell lineages", for the purposes herein, encompasses all hematopoietic precursor cells, other than lymphoid and erythroid blood cell lineages as defined above, and "myelopoiesis" involves the formation of blood cells (other than lymphocytes and erythrocytes).

A "CD34$^+$ cell population" is enriched for hematopoietic stem cells. A CD34$^+$ cell population can be obtained from umbilical cord blood or bone marrow, for example. Human umbilical cord blood CD34$^+$ cells can be selected for using immunomagnetic beads sold by Miltenyi (California), following the manufacturer's directions.

An "AA4$^+$ cell population" is enriched for hematopoietic stem cells. An AA4$^+$ cell population can be obtained from fetal liver for example. AA4$^+$ cells can be selected by immunoadherent panning, for example, with an antibody such as AA4.1.

A "Lin$^{lo}$Sca$^+$", "cell population" or "AA4$^+$Sca$^+$ cell population" is enriched for hematopoietic stem cells. Such populations can be obtained from bone marrow or fetal liver, respectfully, for example. Lin$^{lo}$Sca$^+$ cells or AA4$^+$Sca$^+$ cells can be selected by cell sorting after staining with an antibody to the Sca-1 antigen (Ly6A/E), for example, the Ly6A/E phycoerythrin conjugate from Pharmingen (San Diego, Calif.).

A "flASK cell population" is highly enriched for hematopoietic stem cells from fetal liver. A flASK cell is a fetal liver, AA4$^+$, Sca$^+$, kit$^+$ cell. flASK cells can be selected by cell sorting after staining, for example, with antibodies.

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween®, Pluronic® or polyethylene glycol (PEG).

The term "cytokine" is a generic term for proteins released by one cell population which act on another cell as intercellular mediators. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen, OB protein; tumor necrosis factor-α and -β; mullerian-inhibiting substance; mouse gonadotropinassociated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulatingfactors (CSFs) such as macrophage-CSF(M-CS F); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; and other polypeptide factors including leukemia inhibitory factor (LIF) and kit ligand (KL). As used herein, the term cytokine includes proteins from natural sources or from recombinant cell culture and biologically active equivalents of the native sequence cytokines.

A "lineage-specific cytokine" is one which acts on relatively committed cells in the hematopoietic cascadeand gives rise to an expansion in blood cells of a single lineage. Examples of such cytokines include EPO, TPO, and G-CSF.

"Treatment" refers to both therapeutictreatment and prophylacticor preventative measures. Those in need of treatment include those already with the disease or disorder as well as those in which the disease or disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

By "solid phase" is meant a non-aqueous matrix to which a reagent of interest (e.g., the Wnt polypeptide or an antibody thereto) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

II. Modes for Carrying Out the Invention

The present invention is based on the discovery of the uses of Wnt polypeptidesto enhance hematopoiesis. The experiments described herein demonstrate that Wnts function as hematopoietic regulatory factors which appear to play a role in enhancing proliferation, differentiation and/or maintenance of hematopoietic cells. In particular, Wnts have been found to be present in enriched human stem cell populations, and Wnts may be used to stimulate proliferation of hematopoietic stem cells/progenitor cells. Other uses for these polypeptides will be apparent from the following discussion. A description follows as to how Wnt genes and polypeptides may be prepared.

A. Preparation of Wnt Genes and Gene Products

Most of the discussion below pertains to recombinant production of Wnt genes and gene products by culturing cells transformed with a vector containing Wnt polypeptide-encoding nucleic acid and recovering the polypeptide from the cell culture.

1. Isolation of DNA Encoding Wnt Polypeptide

The DNA encoding Wnt polypeptide may be obtained from any cDNA library prepared from tissue believed to possess the Wnt polypeptide mRNA and to express it at a detectable level. Accordingly, Wnt polypeptide DNA can be conveniently obtained from a cDNA library prepared from mammalian fetal liver or fetal brain. The Wnt polypeptide-encoding gene may also be obtained from a genomic library or by oligonucleotide synthesis.

Libraries are screened with probes (such as antibodies to the Wnt polypeptide, or oligonucleotides of about 20–80 bases) designed to identify the gene of interest or the protein encoded by it. Screening the cDNA or genomic library with the selected probe may be conducted using standard procedures as described in chapters 10–12 of Sambrook et at, *Molecular Cloning: A Laboratory Manual* (New York: Cold Spring Harbor Laboratory Press, 1989). An alternative means to isolate the gene encoding Wnt polypeptide is to use PCR methodology as described in section 14 of Sambrook et at, supra.

A preferred method of practicing this invention is to use carefully selected oligonucleotide sequences to screen cDNA librariesfrom various human tissues, preferably human fetal liver. The oligonucleotide sequences selected as probes should be of sufficient length and sufficiently unambiguous that false positives are minimized.

The oligonucleotidemust be labeled such that it can be detected upon hybridizationto DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

Amino acid sequence variants of Wnt polypeptide are prepared by introducing appropriate nucleotide changes into the Wnt polypeptide DNA, or by synthesis of the desired Wnt polypeptide. Such variants represent insertions, substitutions, and/or specified deletions of, residues within or at one or both of the ends of the amino acid sequence of a naturally occurring human Wnt polypeptide. Preferably, these variants represent insertions and/or substitutions within or at one or both ends of the mature sequence, and/or insertions, substitutions and/or specified deletions within or at one or both of the ends of the signal sequence of the Wnt polypeptide. Any combination of insertion, substitution, and/or specified deletion is made to arrive at the final construct, provided that the final construct possesses the desired biological activity as defined herein. The amino acid changes also may alter post-translational processes of the Wnt polypeptide, such as changing the number or position of glycosylation sites, altering the membrane anchoring characteristics, and/or altering the intracellular location of the Wnt polypeptide by inserting, deleting, or otherwise affecting the leader sequence of the Wnt polypeptide.

Variations in the native sequence as described above can be made using any of the techniques and guidelines for conservative and non-conservative mutations set forth in U.S. Pat. No. 5,364,934. These include oligonucleotide-mediated (site-directed) mutagenesis, alanine scanning, and PCR mutagenesis. See also, for example, Table I therein and the discussion surrounding this table for guidance on selecting amino acids to change, add, or delete.

2. Insertion of Nucleic Acid into Replicable Vector

The nucleic acid (e.g., cDNA or genomic DNA) encoding the Wnt polypeptide is inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

a. Signal sequence component

The Wnt polypeptide useful in hematopoiesis according to the invention may be produced recombinantly not only directly, but also as a fusion polypeptide with a heterologous polypeptide, which is preferably a signal sequence or other polypeptide having a specific cleavage site at the N-terminus of the mature protein or polypeptide. In general, the signal sequence may be a component of the vector, or it may be a part of the Wnt polypeptide DNA that is inserted into the vector. The heterologous signal sequence selected preferably is one that is recognized and processed (i.e., cleaved by a signal peptidase) by the host cell. For prokaryotic host cells that do not recognize and process the native Wnt polypeptide signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including Saccharomyces and Kluyveromyces α-factor leaders, the latter described in U.S. Pat. No. 5,010,182 issued Apr. 23, 1991), or acid phosphatase leader, the *C. albicans* glucoamylase leader (EP 362,179 published Apr. 4, 1990), or the signal described in WO 90/13646 published Nov. 15, 1990. In mammalian cell expression the native signal sequence (e.g., the Wnt polypeptide presequence that normally directs secretion of Wnt polypeptide from human cells in vivo) is satisfactory, although other mammalian signal sequences may be suitable, such as signal sequences from other animal Wnt polypeptide, and signal sequences from secreted polypeptides of the same or related species, as well as viral secretory leaders, for example, the herpes simplex gD signal.

The DNA for such precursor region is ligated in reading frame to DNA encoding the mature Wnt polypeptide.

b. Origin of replication component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example. a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of Wnt polypeptide DNA. However, the recovery of genomic DNA encoding Wnt polypeptide is more complex than that of an exogenously replicated vector because restriction enzyme digestion is required to excise the Wnt polypeptide DNA.

c. Selection gene component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the Wnt polypeptide nucleic acid, such as DHFR or thymidine kinase. The mammalian cell transformantsare placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes Wnt polypeptide. Amplification is the process by which genes in greater demand for the production of a protein critical for growth are reiterated in tandem within the chromosomes of successive generations of recombinant cells. Increased quantities of Wnt polypeptide are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub et al., *Proc. Nati. Acad. Sci. USA,* 77: 4216 [1980]. The transformed cells are then exposed to increased levels of methotrexate. This leads to the synthesis of multiple copies of the DHFR gene, and, concomitantly, multiple copies of other DNA comprising the expression vectors, such as the DNA encoding Wnt polypeptide. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) tranrsformed or co-transformed with DNA sequences encoding Wnt polypeptide, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature,* 282:39–43 [1979]). The trp1 gene provides a selection marker for a mutant strain of yeast lacking the ability to grow in tryptophan, for example, ATCC No. 44076 or PEP4-1. Jones, *Genetics,* 85(1):23–33 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmidpKD1 can be used for transformation of Kluyveromyces yeasts. Bianchi et al., *Curr. Genet.,* 12: 185 [1987]. More recently, an expression system for large-scale production of recombinant calf chymosin was reported for *K. lactis.* Van den Berg, *Bio/Technology,* 8: 135 [1990]. Stable multicopy expression vectors for secretion of mature recombinant human serum albumin by industrial strains of Kluyveromyces have also been disclosed. Fleer et al., *Bio/Technology,* 9: 968–975 [1991].

d. Promoter Component

Expression and cloning vectors usually contain a promoter that is recognized by the host organism and is operably linked to the Wnt polypeptide nucleic acid. Promoters are untranslated sequences located upstream (5') to the start codon of a structural gene (generally within about 100 to 1000 bp) that control the transcription and translation of particular nucleic acid sequence, such as the Wnt polypeptide nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to Wnt polypeptide-encoding DNA by removing the promoter from the source DNA by restriction enzyme,digestion and inserting the isolated promoter sequence into the vector. Both the native Wnt polypeptide promoter sequence and many heterologous promoters may be used to direct amplification and/or expression of the Wnt polypeptide DNA. However, heterologous promoters are preferred, as they generally permit greater transcription and higher yields of Wnt polypeptide as compared to the native Wnt polypeptide promoter.

Promoters suitable for use with prokaryotic hosts include the β-lactamase and lactose promoter systems (Chang et al., *Nature,* 275:617–624 [1978]; Goeddel al., *Nature,* 281: 544 [1979]), alkaline phosphatase, a tryptophan (trp) promoter system (Goeddel, *Nucleic Acids Res.,* 8: 4057 [1980]; EP 36,776), and hybrid promoters such as the tac promoter. deBoer et al., *Proc. Natl. Acad. Sci. USA,* 80: 21–25 [1983]. However, other known bacterial promoters are suitable. Their nucleotide sequences have been published, thereby enabling a skilled worker operably to ligate them to DNA encoding Wnt polypeptide (Siebenlist et al., *Cell,* 20: 269 [1980]) using linkers or adaptorsto supply any required restriction sites. Promoters for use in bacterial systems also will contain a Shine-Dalgarno (S.D.) sequence operably linked to the DNA encoding Wnt polypeptide.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglyceratekinase (Hitzeman et al., *J. Biol. Chem.,* 255: 12073–12080 [1980]) or other glycolytic enzymes (Hess et al., *J. Adv. Enzyme Reg.,* 7: 149 [1968]; Holland, *Biochemistry,* 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradativeenzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Wnt polypeptide transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the Wnt polypeptide sequence, provided such promoters are compatible with the host cell systems.

The early and late promoters of the SV40 virus are conveniently obtained as an SV40 restriction fragment that also contains the SV40 viral origin of replication. Fiers et al., *Nature* 273:113(1978); Mulligan et al., *Science,*209: 1422–1427[1980]; Pavlakis et al., *Proc. Natl. Acad. Sci. USA* 78: 7398–7402 [1981]. The immediate early promoter of the human cytomegalovirus is conveniently obtained as a HindIII E restriction fragment. Greenaway et al., *Gene,* 18: 355–360 [1982]. A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295: 503–508 [1982] on expressing cDNA encoding immune interferon in monkey cells; Reyes et al., *Nature,* 297: 598–601 [1982] on expression of human β-interferon cDNA in mouse cells under the control of a thymidine kinase promoter from herpes simplex virus; Canaani et al., *Proc. Natl. Acad. Sci. USA,* 79: 5166–5170 [1982] on expression of the human interferon β1 gene in cultured mouse and rabbit cells; and Gorman et al, *Proc. Natl. Acad. Sci. USA,* 79: 6777–6781 [1982] on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

e. Enhancer element component

Transcription of a DNA encoding the Wnt polypeptide useful in hematopoiesis according to the invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA* 78:464–468 [1981]) and 3' (Lusky et al., *Mol. Cell Bio.,* 3: 1108 [1983]) to the transcription unit, within an intron (Banerji et al., *Cell,* 33: 729 [1983]), as well as within the coding sequence itself. Osborne et al., *Mol. Cell Bio.,* 4:1293 [1984]). Many enhancersequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the Wnt polypeptide-encoding sequence, but is preferably located at a site 5' from the promoter.

f. Transcription termination component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding Wnt polypeptide.

g. Construction and analysis of vectors

Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9: 309 [1981] or by the method of Maxam et al., *Methods in Enzymology,* 65: 499 [1980].

h. Transient expression vectors

Particularly useful in the practice of this invention are expression vectors that provide for the transient expression in mammalian cells of DNA encoding Wnt polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of Wnt polypeptide that are biologically active Wnt polypeptide.

i. Suitable exemplary vertebrate cell vectors

Other methods, vectors, and host cells suitable for adaptation to the synthesis of Wnt polypeptide in recombinant vertebrate cell culture are described in Gething et al., *Nature* 293:620–625 (1981); Mantei et al., *Nature* 281: 40–46 [1979]; EP 117,060; and EP 117,058. A particularly useful plasmid for mammalian cell culture expression of Wnt polypeptide is pRK5 (EP 307,247) or pSVI6B. WO 91/08291 published Jun 13, 1991.

3. Selection and Transformation of Host Cells

Suitable host cells for cloning or expressing the DNA in the vectors herein are the prokaryote, yeast, or highereukaryotecells described above. Suitable prokaryotes for this purpose include eubacteria, such as Gram-negative or Gram-positive organisms, for example, Enterobacteriaceae such as Escherichia, e.g., *E. coli,* Enterobacter, Erwinia, Klebsiella, Proteus, Salmonella, e.g., *Salmonella typhimurium,* Serratia, e.g., *Serratia marcescans,* and Shigella, as well as Bacilli such as *B. subtilis* and *B. licheniformis* (e.g., *B. licheniformis* 41 P disclosed in DD 266,710 published Apr. 12, 1989), Pseudomonas such as *P. aeruginosa,* and Streptomyces. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a particularly preferred host or parent host because it is a common host strain for recombinant DNA product fermentations. Preferably, the host cell should secrete minimal amounts of proteolyticenzymes. For example, strain W3110 may be modified to effect a genetic mutation in the genes encoding proteins, with examples of such hosts including *E. coli* W3110 strain 27C7. The complete genotype of 27C7 is tonAα ptr3 phoAΔE15Δ(argF-lac)169ompTΔ degP41kan$^r$. Strain 27C7 was deposited on Oct. 30, 1991 in the American Type Culture Collection as ATCC No. 55,244. Alternatively, the strain of *E. coli* having mutant periplasmicprotease disclosed in U.S. Pat. No. 4,946, 783 issued Aug. 7, 1990 may be employed. Alternatively still, methods of cloning, e.g., PCR or other nucleic acid polymerase reactions, are suitable. In addition to prokaryotes, eukaryotic microbes such as filamentous fungi or yeast are suitable cloning or expression hosts for Wnt polypeptide-encoding vectors. *Saccharomy cescerevisiae,* or common baker's yeast, is the most commonly used among lower eukaryotic host microorganisms However, a number of other genera, species, and strains are commonly available and useful herein, such as *Schizosaccharomyces pombe* (Beach et al., *Nature,* 290: 140 [1981]; EP 139,383 published May 2, 1985); Kluyveromyces hosts (U.S. Pat. No. 4,943,529; Fleer et al., supra) such as, e.g., *K. lactis* (MW98-8C, CBS683, CBS4574), *K. fragilis* (ATCC 12,424), *K. bulgaricus* (ATCC 16,045), *K. wickeramii* (ATCC 24,178), *K waltii* (ATCC 56,500), *K. drosophilarum* (ATCC 36,906; Van den Berg et al., supra), *K. thermotolerans,* and *K. marxianus; yarrowia* (EP 402,226); *Pichia pastoris* (EP 183,070; Sreekrishna et al., *J. Basic Microbiol.* 28:265–278 (1988)); Candida; *Trichoderma reesia* (EP 244,234); *Neurospora crassa* (Case et al., *Proc. Natl. Acad. Sci. USA* 76:5259–5263 (1979)); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.* 112:284–289 (1983); Tilburn et al., *Gene* 26:205–221 (1983); Yelton et al., *Proc. Natl. Acad. Sci. USA,* 81 1470–1474 [1984]) and A. niger. Kelly et al., *EMBO J.,* 4: 475–479 [1985].

Suitable host cells for the expression of glycosylated Wnt polypeptide are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology,* 6: 47–55 [1988]; Miller et al., in *Genetic Engineering,* Setlow et al., eds., Vol. 8 (Plenum Publishing, 1986), pp. 277–279; and Maeda et al., *Nature,* 315: 592–594 [1985]. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens;* which has been previously manipulated to contain the Wnt polypeptide-encoding DNA. During incubation of the plant cell culture with *A. tumefaciens,* the DNA encoding the Wnt polypeptide is transferred to the plant cell host such that it is transfected, and will, under appropriate conditions, express the Wnt polypeptide-encoding DNA. In addition, regulatory and signal sequences compatible with plant cells are available, such as the nopaline synthase promoter and polyadenylation signal sequences. Depicker et al, *J. Mol. Appl. Gen.,* 1: 561 [1982]. In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

However, interest has been greatest in vertebrate cells, and propagation of vertebrate cells in culture (tissue culture) has become a routine procedure. See, e.g., *Tissue Culture,* Academic Press, Kruse and Patterson, editors (1973). Examples of useful mammalian host cell lines are monkey kidney CV1 line transformed by SV40 (COS-7, ATCC CRL 1651); human embryonic kidney line (293 or 293 cells subcdoned for growth in suspension culture, Graham et al., *J. Gen Virol* 36: 59 [1977]); baby hamster kidney cells (BHK, ATCC CCL 10); Chinese hamster ovary cells/-DHFR (CHO, Urlaub et al., *Proc. Natl. Acad. Sci. USA,* 77: 4216 [1980]); mouse sertoli cells (TM4, Mather, *Biol. Reprod.,* 23:243–251 (1980)); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Matheret al., *Annals N.Y. Acad. Sci.,* 383: 44–68 [1982]); MRC 5 cells; FS4 cells; and a human hepatoma line (Hep G2).

Host cells are transfected and preferably transformed with the above-described expression or cloning vectors for Wnt polypeptide production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomalelement or by chromosomal integrant. Depending on the host cell used, transformation is done using standard techniques appropriate to such cells. The calcium treatment employing calcium chloride, as described in section 1.82 of Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene,* 23:315(1983) and WO 89/05859 published Jun. 29, 1989. In addition, plants may be transfected using ultrasound treatment as described in WO 91/00358 published Jan. 10, 1991.

For mammalian cells without such cell walls, the calcium phosphate precipitation method of Graham et al., *Virology,* 52: 456–457 [1973] is preferred. General aspects of mammalian cell host system transformations have been described in U.S. Pat. No. 4,399,216 issued Aug. 16, 1983. Transformationsinto yeast are typically carried out according to the method of Van Solingen et al., *J. Bact.,* 130:946 [1977] and Hsiao et al., *Proc. Natl. Acad. Sci. USA,* 76: 3829 [1979]. However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology,* 185: 527–537 [1990] and Mansour et al., *Nature,* 336: 348–352 [1988].

4. Culturing the Host Cells

Prokaryotic cells used to produce the Wnt polypeptide useful according to the invention are cultured in suitable media as described generally in *Sambrook* et al., supra.

The mammalian host cells used to produce the Wnt polypeptide of this invention may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. In addition, any of the media described in Ham et al., *Meth. Enz.,* 58: 44 [1979], Barnes et al., *Anal. Biochem.,* 102: 255 [1980], U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as GENTAMYCIN™ drug), trace elements (defined as inorganic compounds usually present at final concentrations in the micromolarrange), and glucose oran equivalent energy source. Any other necessary supplements may also be included at appropriate concentrations that would be known to those skilled in the art. The culture conditions, such as temperature, $pH_1$ and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach,* M. Butler, ed. (IRL Press, 1991).

The host cells referred to in this disclosure encompass cells in culture as well as cells that are within a host animal.

5. Detecting Gene Amplification/Expression

Gene amplification and/or expression may be measured in a sample directly, for example, by conventional Southern blotting, Northern blotting to quantitate the transcription of mRNA (Thomas, *Proc Natl. Acad. Sci. USA*, 77: 5201–5205 [1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734–738 [1981].

Antibodies useful for immunohistochemical staining and/or assay of sample fluids may be either monoclonal or polyclonal, and may be prepared as described herein.

6. Purification of Wnt Polypeptide

Wnt polypeptide may be recovered from the culture medium as a secreted polypeptide, although it is preferentially recovered from host cell lysates. If the Wnt polypeptide is membrane-bound, it can be released from the cell surface using suitable agents, including enzyms or detergents (e.g. Triton®X-100), for example, suramin, PMA, heparin, Heparinase I and III, plasmin, n-Octyl-beta-D-glucoside, Pl-specific- and PC-specific-phospholipase C and TNF-alpha.

When Wnt polypeptide is produced in a recombinant cell other than one of human origin, the Wnt polypeptide is completely free of proteins or polypeptides of human origin. However, it is necessary to purify Wnt polypeptide from recombinant cell proteins or polypeptides to obtain preparations that are substantially homogeneous as to Wnt polypeptide. As a first step, the culture medium or lysate is centrifuged to remove particulate cell debris. Wnt polypeptide thereafter is purified from contaminant soluble proteins and polypeptides, with the following procedures being exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex®G-75; and protein A Sepharose™ columns to remove contaminants such as IgG.

Wnt polypeptide variants in which residues have been deleted, inserted, or substituted are recovered in the same fashion as native sequence Wnt polypeptide, taking account of any substantial changes in properties occasioned by the variation. Immunoaffinity columns such as a rabbit polyclonal anti-Wnt polypeptide column can be employed to absorb the Wnt polypeptide variant by binding it to at least one remaining immune epitope.

A protease inhibitor such as phenyl methyl sulfonyl fluoride (PMSF) also may be useful to inhibit proteolytic degradation during purification, and antibiotics may be included to prevent the growth of adventitious contaminants.

7. Covalent Modifications

Covalent modifications of Wnt polypeptide are included within the scope of this invention. Both native sequence Wnt polypeptide and amino acid sequence variants of the Wnt polypeptide may be covalently modified. One type of covalent modification of the Wnt polypeptide is introduced into the molecule by reacting targeted amino acid residues of the Wnt polypeptide with an organic derivatizing agent that is capable of reacting with selected side chains or the N- or C-terminal residues of the Wnt polypeptide.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleim ides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed under alkaline conditions because of the high $pK_a$ of the guanidine functional group. Furthermore, these reagents may react with the groups of lysine as well as with the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method being suitable.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking Wnt polypeptide to a water-insoluble support matrix or surface for use in the method for purifying anti-Wnt polypeptide antibodies, and vice-versa. Commonly used crosslinking agents include, e.g., 1,1-bis(diazoacetyl)-2-phenylethane, glutaraldehyde, N-hydroxysuccinimide esters, for example, esters with 4-azido-salicylic salicylic acid, homobifunctionalimidoesters, including disuccinimidyl esters such as 3,3'-dithiobis-(succinimidylpropionate), and bifunctional maleimides such as bis-N-maleimido-1,8-octane. Derivatizing agents such as methyl-3-((p-azidophenyl)dithio)propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties* W. H. Freeman & Co., San Francisco, pp. 79–86 (1983)), acetylation of the N-terminal amine, and amidation of any C-terminal carboxyl group.

Another type of covalent modification of the Wnt polypeptide included within the scope of this invention comprises altering the native glycosylation pattern of the polypeptide. By altering is meant deleting one or more carbohydrate moieties found in native Wnt polypeptide, and/or adding one or more glycosylation sites that are not present in the native Wnt polypeptide.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxylamino acid, most commonly serine or threonine, although 5-hydroxyproline or 5-hydroxylysine may also be used.

Addition of glycosylation sites to the Wnt polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native Wnt polypeptide sequence (for O-linked glycosylation sites). For ease, the Wnt polypeptide amino acid sequence is preferably altered through changes at the DNA level, particularly by mutating the DNA encoding the Wnt polypeptide at preselected bases such that codons are generated that will translate into the desired amino acids. The DNA mutation(s) may be made using methods described above and in U.S. Pat. No. 5,364,934, supra.

Another means of increasing the number of carbohydrate moieties on the Wnt polypeptide is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin et al., *CRC Crit. Rev. Biochem.* 259–306 (1981).

Removal of carbohydrate moieties present on the Wnt polypeptide may be accomplished chemically or enzymatically. Chemical deglycosylation requires exposure of the polypeptide to the compound trifluoromethanesulfonicacid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al, *Arch. Biochem. Biophys.* 259:52 (1987) and by Edge et al., *Anal. Biochem.* 118:131 (1981). Enzymatic cleavage of carbohydrate moieties on polypeptides can be achieved by the use of a variety of endo- and exo-glycosidases as described by Thotakura et al., *Meth. EnzymoL* 138:350 (1987).

Glycosylation at potential glycosylation sites may be prevented by the use of the compound tunicamycin as described by Duksin et al., *J. Biol. Chem.* 257:3105 (1982). Tunicamycin blocks the formation of protein-N-glycoside linkages.

Another type of covalent modification of Wnt polypeptide comprises linking the Wnt polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Since it is often difficult to predict in advance the characteristics of a variant Wnt polypeptide, it will be appreciated that some screening of the recovered variant will be needed to select the optimal variant. A change in the immunological character of the Wnt polypeptide molecule, such as affinity for a given antibody, is also able to be measured by a competitive-type immunoassay. The Wnt polypeptide variant is assayed for changes in the ability of the protein to induce cell proliferation in the assays of Example 2. Other potential modifications of protein or polypeptide properties such as redox or thermal stability, hydrophobicity, susceptibility to proteolytic degradation, or the tendency to aggregate with carriers or into multimers are assayed by methods well known in the art.

8. Epitope-Tagged Wnt Polypeptide

This invention encompasses chimeric polypeptides comprising Wnt polypeptide fused to a heterologous polypeptide. A chimeric Wnt polypeptide is one type of Wnt polypeptide variant as defined herein. In one preferred embodiment, the chimeric polypeptide comprises a fusion of the Wnt polypeptide with a tag polypeptide which provides an epitope to which an anti-tag antibody can selectively bind. The epitope tag is generally provided at the amino- or carboxyl- terminus of the Wnt polypeptide. Such epitope-tagged forms of the Wnt polypeptide are desirable as the presence thereof can be detected using a labeled antibody against the tag polypeptide. Also, provision of the epitope tag enables the Wnt polypeptide to be readily purified by affinity purification using the anti-tag antibody. Affinity purification techniques and diagnostic assays involving antibodies are described later herein. Tag polypeptides and their respective antibodies are well known in the art. Examples include the Herpes Simplex virus glycoprotein D (gD) tag and its antibody (Pennica et al., supra); the his tag, for example his$_6$ (Hengen, *Trends Biochem. Sci.,* 20: 285–286 [1995] and Pennica et al., *J. Biol. Chem.,* 270: 10915–10922 [1995]); the flu HA tag polypeptide and its antibody 12CA5 (Field et al., *Mol. Cell. Biol.,* 8: 2159–2165 [1988]); the c-myc tag and the 8F9, 3C7, 6E10, G4, B7 and 9E10 antibodies thereto (Evan et al., *Molecular and Cellular Biology,* 5: 3610–3616 [1985]; and Paborsky et al., *Protein Engineering,* (6): 547–553 [1990]). Other tag polypeptides have been disclosed. Examples include the Flag-peptide (Hopp et al., *BioTechnology,* 6: 1204–1210 [1988]); the KT3 epitope peptide (Martin et al., *Science,* 255: 192–194 [1992]); an α-tubulin epitope peptide (Skinneret al., *J. Biol. Chem.,* 266: 14163–14166 [1991]); and the T7 gene 10 protein peptide tag. Lutz-Freyermuth et al., *Proc. Natl. Acad. Sci. USA,* 87: 6393–6397 [1990]. Once the tag polypeptide has been selected, an antibody thereto can be generated using the techniques disclosed herein.

The general methods suitable for the construction and production of epitope-tagged Wnt polypeptide are the same as those disclosed hereinabove. Wnt polypeptide-tag polypeptide fusions are most conveniently constructed by fusing the cDNA sequence encoding the Wnt polypeptide portion in-frame to the tag polypeptide DNA sequence and expressing the resultant DNA fusion construct in appropriate host cells. Ordinarily, when preparing the Wnt polypeptide-tag polypeptide chimeras of the present invention, nucleic acid encoding the Wnt polypeptide will be fused at its 3'end to nucleic acid encoding the N-terminus of the tag polypeptide, however 5' fusions are also possible.

Epitope-tagged Wnt polypeptide can be conveniently purified by affinity chromatography using the anti-tag antibody. The matrix to which the affinity antibody is attached is most often agarose, but other matrices are available (e.g. controlled pore glass or poly(styrenedivinyl)benzene). The epitope-taggedwnt polypeptide can be eluted from the affinity column by varying the buffer pH or ionic strength or adding chaotropic agents, for example.

9. Wnt Polypeptide Immunoadhesins

Chimeras constructed from a receptor sequence linked to an appropriate immunoglobulin constantdomain sequence (immunoadhesins)are known in the art. Immunoadhesins reported in the literature include fusions of the T cell receptor* (Gascoigne et al., *Proc. Nat. Acad. Sci. USA* 84: 2936–2940 (1987)); CD4* (Capon et al., *Nature* 337: 525–531 (1989); Traunecker et al., *Nature* 339: 68–70 (1989); Zettlmeissl et al., *DNA Cell Biol. USA* 9: 347–353 (1990); Byrn et al, *Nature* 344: 667–670 (1990)); L-selectin (homing receptor) ((Watson et al., *J. Cell. Biol.* 110:2221–2229 (1990); Watson et al., *Nature* 349:164–167 (1991)); CD44* (Aruffo et al., *Cell*61:1303–1313(1990)); CD28* and B7* (Lisley et al., *J. Exp. Med.* 173: 721–730 (1991)); CTLA4* (Lisley et al., *J. Exp. Med.* 174: 561–569 (1991)); CD22* (Stamenkovic et al., *Cell* 66:1133–1144 (1991)); TNF receptor (Ashkenazi et al, *Proc. Natl. Acad. Sci. USA* 88: 10535–10539 (1991); Lesslauer et al., *Eur. J. Immunol* 27: 2883–2886 (1991); Peppel et al., *J. Exp. Med.* 174:1483–1489 (1991)); NP receptors (Bennett et al., *J. Biol. Chem.* 266:23060–23067 (1991)); and IgE receptor α* (Ridgway et al., *J. Cell. Biol.* 115:abstr. 1448 (1991)), where the asterisk (*) indicates that the receptor is member of the immunoglobulin superfamily.

The simplest and most straightforward immunoadhesin design combines the binding region(s) of the "adhesin" protein with the hinge and Fc regions of an immunoglobulin heavy chain. Ordinarily, when preparing the Wnt polypeptide-immunoglobulinchimeras of the present invention, nucleic acid encoding Wnt polypeptide will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain.

The precise site at which the fusion is made is not critical; particular sites are well known and may be selected in order to optimize the biological activity, secretion or binding characteristics of the Wnt polypeptide-immunoglobulin chimeras.

In some embodiments, the Wnt polypeptide-immunoglobulin chimeras are assembled as monomers, or hetero- or homo-multimers, and particularly as dimers or tetramers, essentially as illustrated in WO 91/08298.

In a preferred embodiment, the Wnt polypeptide sequence is fused to the N-terminus of the C-terminal portion of an antibody (in particularthe Fc domain), containing the effector functions of an immunoglobulin, e.g. immunoglobulin Gl (IgG1). It is possible to fuse the entire heavy chain constant region to the Wnt polypeptide sequence. However, more preferably, a sequence beginning in the hinge region just upstream of the papain cleavage site (which defines IgG Fc chemically; residue 216, taking the first residue of heavy chain constant region to be 114, or analogous sites of other immunoglobulins) is used in the fusion. In a particularly preferred embodiment, the Wnt polypeptide amino acid sequence is fused to the hinge region, CH2 and CH3, or the CH1, hinge, CH2 and CH3 domains of an IgG1, lgG2, or IgG3 heavy chain. The precise site at which the fusion is made is not critical, and the optimal site can be determined by routine experimentation.

In some embodiments, the Wnt polypeptide-immunoglobulin chimeras are assembled as multimers, and particularly as homo-dimers or -tetramers. Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamerof basic four units held together by disulfide bonds. IgA globulin, and occasionally IgG globulin, may also exist in multimeric form in serum. In the case of multimer, each four unit may be the same or different.

Various exemplary assembled Wnt polypeptide-immunoglobulinchimeras within the scope herein are schematically diagrammed below:

(a) $AC_L\text{-}AC_L$;
(b) $AC_H\text{-}(AC_H, AC_L\text{-}AC_H, AC_L\text{-}V_HC_H, \text{ or } V_LC_L\text{-}AC_H)$;
(c) $AC_L\text{-}AC_H\text{-}(AC_L\text{-}AC_H, AC_L\text{-}V_HC_H, V_LC_L\text{-}AC_H, \text{ or } V_LC_L\text{-}V_HC_H)$;
(d) $AC_{L\text{-}VH}C_H\text{-}(AC_H, \text{ or } AC_L\text{-}V_HC_H, \text{ or } V_LC_L\text{-}AC_H)$;
(e) $V_LC_L\text{-}AC_H\text{-}(AC_L\text{-}V_HC_H, \text{ or } V_LC_L\text{-}AC_H)$; and
(f) $(A\text{-}Y)_n\text{-}(V_LC_L\text{-}V_HC_H)_2$, wherein each A represents identical or different Wnt polypeptide or amino acid sequences;

$V_L$ is an immunoglobulin light chain variable domain;

$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the Wnt polypeptide sequence can be inserted between immunoglobulin heavy chain and light chain sequences such that an immunoglobulin comprising a chimeric heavy chain is obtained. In this embodiment, the Wnt polypeptide sequence is fused to the 3' end of an immunoglobulin heavy chain in each arm of an immunoglobulin, either between the hinge and the CH2 domain, or between the CH2 and CH3 domains. Similar constructs have been reported by Hoogenboom et al, *Mol. Immunol.*, 28:1027–1037 (1991).

Although the presence of an immunoglobulin light chain is not required in the immunoadhesins of the present invention, an immunoglobulin light chain might be present either covalently associated to an Wnt polypeptide-immunoglobulin heavy chain fusion polypeptide, or directly fused to the Wnt polypeptide. In the former case, DNA encoding an immunoglobulin light chain is typically coexpressed with the DNA encoding the Wnt polypeptide-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567 issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG1 and IgG3 immunoglobulin sequences is preferred. A major advantage of using IgG1 is that IgG1 immunoadhesins can be purified efficiently on immobilized protein A. In contrast, purification of IgG3 requires protein G, a significantly less versatile medium. However, other structural and functional properties of immunoglobulins should be considered when choosing the Ig fusion partner for a particular immunoadhesin construction. For example, the IgG3 hinge is longer and more flexible, so it can accommodate larger adhesin domains that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit. For immunoadhesins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1m1, is non-immunogenic. In contrast, there are 12 serological-defined allotypes in IgG3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

With respect to the parental immunoglobulin, a useful joining point is just upstream of the cysteines of the hinge that form the disulfide bonds between the two heavy chains. In a frequently used design, the codon for the C-terminal residue of the Wnt polypeptide part of the molecule is placed directly upstream of the codons for the sequence DKTH-TCPPCP (SEQ ID NO:1) of the IgG1 hinge region.

The general methods suitable for the construction and expression of immunoadhesins are the same as those disclosed hereinabove with regard to Wnt polypeptide. Immunoadhesins are most conveniently constructed by fusing the cDNA sequence encoding the Wnt polypeptide portion in-frame to an Ig cDNA sequence. However, fusion to genomic Ig fragments can also be used (see, e.g., Gascoigne et al., *Proc. Natl. Acad. Sci. USA*, 84:2936–2940 (1987); Aruffo et al., *Cell* 61:1303–1313 (1990); Stamenkovic et al., *Cell* 66:1133–1144 (1991)). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The cDNAs encoding the Wnt polypeptide and Ig parts of the immunoadhesin are inserted in tandem into a plasmid vector that directs efficient expression in the chosen host cells. For expression in mammalian cells, pRK5-based vectors (Schall et al., *Cell* 61:361–370 (1990)) and CDM8-based vectors (Seed, *Nature* 329:840 (1989)) can be used. The exact junction can be created by removing the extra sequences between the designed junction codons using oligonucleotide-directed deletional mutagenesis (Zoller et al., *Nucleic Acids Res.* 10:6487 (1982); Capon et al., *Nature* 337:525–531 (1989)). Synthetic oligonucleotides can be used, in which each half is complementary to the sequence on either side of the desired junction; ideally, these are 36 to 48-mers. Alternatively, PCR techniques can be used to join the two parts of the molecule in-frame with an appropriate vector.

The choice of host cell line for the expression of the immunoadhesin depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient immunoadhesin expression. CDM8-based vectors can be used to transfect COS cells by the DEAE-dextran method (Aruffo et al., *Cell* 61:1303–1313 (1990); Zettmeissl et al., *DNA Cell Biol. US* 9:347–353 (1990)). If larger amounts of protein are desired, the immunoadhesin can be expressed after stable transfection of a host cell line. For example, a pRK5-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts (Gascoigne et al., 1987, supra, Martin et al., *J. Virol.* 67:3561–3568 (1993)).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human y1, y2, or y4 heavy chains (Lindmark et al., *J. Immunol. Meth.* 62:1–13 (1983)). Protein G is recommendedfor all mouse isotypes and for human y3 (Guss et al., *EMBO J.* 5:1567–1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins.is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatographyon proteinA or G to purify immunoadhesins. Immunoadhesins behave similarly to antibodiesin thiophilicgel chromatography (Hutchens et al., *Anal. Biochem.* 159:217–226(1986)) and immobilized metal chelate chromatography (AI-Mashikhi et al., *J. Daify Sci.* 71:1756–1763 (1988)). In contrast to antibodies, however, their behavioron ion exchange columns is dictated not only by their isoelectric points, but also by a charge dipole that may exist in the molecules due to their chimeric nature.

If desired, the immunoadhesins can be made bispecific. Thus, the immunoadhesins of the present invention may combine a Wnt polypeptide and a domain, such as the extracellular domain, of another cytokine receptor subunit. Exemplary cytokine receptors from which such bispecific immunoadhesin molecules can be made include TPO (or mpl ligand), EPO, G-CSF, IL-4, IL-7, GH, PRL, IL-3, GM-CSF, IL-5, IL-6, LIF, OSM,CNTF and IL-2 receptors. Alternatively, a Wnt polypeptide may be combined with another cytokine, such as those exemplified herein, in the generation of a bispecific immunoadhesin. For bispecific molecules, trimeric molecules, composed of a chimeric antibody heavy chain in one arm and a chimeric antibody heavy chain-light chain pair in the other arm of their antibody-like structure are advantageous, due to ease of purification. In contrast to antibody-producing quadromas traditionally used for the production of bispecific immunoadhesins, which produce a mixture of ten tetramers, cells transfected with nucleic acid encoding the three chains of a trimeric immunoadhesin structure produce a mixture of only three molecules, and purification of the desired product from this mixture is correspondingly easier.

10. Long Half-Life Derivatives of Wnt Polypeptides

Wnt polypeptide functional derivatives for use in the methods of the present invention include Wnt-immunoglobulin chimeras (immunoadhesins) and other longer half-life molecules.

Other derivatives of the Wnt polypeptides, which possess a longer half-life than the native molecules comprise the Wnt polypeptide or a Wnt-immunoglobulin chimera covalently bonded to a nonproteinaceouspolymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethyleneand polyoxypropylene(Pluronics™); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonicacid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogenous derivatives.

The molecularweight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the Wnt polypeptide or to the Wnt-immunoglobulin chimera though a multifunctional crosslinking agent which reacts with the polymer and one or more amino acid or sugar residues of the Wnt polypeptide or Wnt-immunoglobulin chimera to be linked. However, it is within the scope of the invention to directly crosslink the polymer by reacting a derivatized polymer with the hybrid, or via versa.

The covalent crosslinking site on the Wnt polypeptide or Wnt-immunoglobulin chimera includes the N-terminal amino group and epsilon amino groups found on lysine residues, as well as other amino, imino, carboxyl, sulfhydryl, hydroxyl or other hydrophilic groups. The polymer may be covalently bonded directly to the hybrid without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylcloroformate or P-nitrophenylcloroformate activated PEG). Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase (either of which produces the aldehyde derivative of the carbohydrate), followed by reaction with hydrazide or amino derivatized polymers, in the same fashion as is described by Heitzmann et al., *P.N.A.S.* 71:3537–41 (1974) or Bayer et al., *Methods in Enzymology* 2:308–315 (1979), for the labeling of oligosaccharides with biotin or avidin. Further, other chemical or enzymatic methods which have been used heretofore to link oligosaccharides are particularly advantageous because, in general, there are fewer substitutions than amino acid sites for derivatization, and the oligosaccharide products thus will be more homogenous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

"Water soluble" in reference to the polymer conjugate means that the conjugate is soluble in physiological fluids such as blood.

The degree of substitution with such a polymer will vary depending upon the number of reactive sites on the protein, whether all or a fragment of the protein is used, whether the protein is a fusion with a heterologous protein (e.g. an Wnt-immunoglobulin chimera), the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of cross-linking is easily determined by an experimental matrix in which the time, temperature and other reaction conditions are varied to change the degree of substitution, after which the ability of the conjugates to function in the desired fashion is determined.

The polymer, e.g. PEG, is cross-linked by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal Biochem.* 131:25–33 (1983)) requires high pH (>8.5), which can inactivate proteins. Moreover, since the "activated PEG" intermediate can react with water, a very large molar excess of "activatedPEG" over protein is required. The high concentrationsof PEG required for the carbonyl diimidazole chemistry also led to problems in purification, as both gel filtration chromatography and hydrophilic interaction chromatography are adversely affected. In addition, the high concentrationsof "activated PEG" may precipitate protein, a problem that perse has been noted previously (Davis, U.S. Pat. No. 4,179,337). On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., *J. Polym. Sci. Polym. Chem. Ed.* 22:341–52 (1984)). The use of a Moffatt oxidation, utilizing DMSO and acetic anhydride, obviates this problem. In addition, the sodium borohydride suggested by Royer must be used at high pH and has a significanttendency to reduce disulfide bonds. In contrast, sodium cyanoborohydride, which is effective at neutral pH and has very little tendency to reduce disulfide bonds is preferred.

Functionalized PEG polymers to modify the Wnt polypeptide or Wnt-immunoglobulin chimeras of the present invention are available from Shearwater Polymers, Inc. (Huntsville, Ala.). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (lysine or cysteine), hydrolytic stability and reactivity of the derivatives, stability, toxicity and antigenicity of the linkage, suitability for analysis, etc. Specific instructions for the use of any particular derivative are available from the manufacturer.

The long half-life conjugates of this invention are separated from the unreacted starting materials by gel filtration. Heterologous species of the conjugates are purified from one another in the same fashion. The polymer also may be water-insoluble, as a hydrophilic gel.

The conjugates may also be purified by ion-exchange chromatography. The chemistry of many of the electrophilically activated PEG's results in a reduction of amino group charge of the PEGylated product. Thus, high resolution ion exchange chromatography can be used to separate the free and conjugated proteins, and to resolve species with different levels of PEGylation. In fact, the resolution of different species (e.g. containing one or two PEG residues) is also possible due to the difference in the ionic properties of the unreacted amino acids.

B. Therapeutic Uses for the Wnt Polypeptide

The Wnt polypeptide and Wnt polypeptide gene are believed to find therapeutic use for administration to a mammal in the treatment of diseases or disorders characterized by a decrease in hematopoietic cells. Examples of these diseases or disorders include: anemia (including macrocytic and aplastic anemia); thrombocytopenia; hypoplasia; disseminated intravascular coagulation (DIC); myelodysplasia; immune (autoimmune) thrombocytopenic purpura (ITP); and HIV induced ITP. Additionally, these Wnt polypeptide molecules may be useful in treating patients having suffered a hemorrhage. Wnt polypeptide and Wnt polypeptide gene which lead to an increase in hematopoietic cell proliferation may also be used to enhance repopulation of mature blood cell lineages in cells having undergone chemo- or radiation therapy or bone marrow transplantation therapy. Generally, these molecules are expected to lead to an enhancement of the proliferation, differentiation and/or maintenance of primitive hematopoietic cells.

The Wnt polypeptide may be administered alone or in combination with one or more cytokines, including growth factors or antibodies in the above-identified clinical situations. This may facilitate an effective lowering of the dose of Wnt polypeptide. Suitable dosages for such additional molecules will be discussed below.

In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA, 83:4143–4146 (1986)). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11:205–210 (1993)). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem. 262:4429–4432 (1987); and Wagner et al., Proc. Natl. Acad. Sci. USA 87:3410–3414 (1990). For review of the currently known gene marking and gene therapy protocols see Anderson et al, Science 256:808–813 (1992).

For therapeutic applications, the Wnt polypeptide useful according to the invention are administered to a mammal, preferably a human, in a physiologically acceptable dosage form, including those that may be administered to a human intravenously as a bolus or by continuous infusion over a period of time. Alternative routes of administration include intramuscular, intraperitoneal, intra-cerebrospinal, subcutaneous, intra-articular, intrasynovial, intrathecal, oral, topical, or inhalation routes. The Wnt polypeptides also are suitably administered by intratumoral, peritumoral, intralesional, or perilesional routes or to the lymph, to exert local as well as systemic therapeutic effects.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of Wnt polypeptides include polysaccharidessuch as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations. The Wnt polypeptide will typically be formulated in such vehicles at a concentration of about 0.1 mg/ml to 100 mg/ml.

Suitable examples of sustained-release preparations include semipermeable matrices of solid hydrophobic polymers containing the Wnt polypeptide, which matrices are in the form of shaped articles, e.g. films, or microcapsules. Examples of sustained-release matrices include polyesters, hydrogels (for example, poly(2-hydroxyethyl-methacrylate) as described by Langer et aL, supra and Langer, supra, or poly(vinylalcohol), polylactides (U.S. Pat. No. 3,773,919), copolymers of L-glutamic acid and γ ethyl-L-glutamate (Sidman et al, supra), non-degradable ethylene-vinyl acetate (Langer et al., supra), degradable lactic acid-glycolic acid copolymers such as the Lupron Depot™ (injectable microspheres composed of lactic acid-glycolicacid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated Wnt polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S-S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release Wnt polypeptide compositions also include liposomally entrapped polypeptides. Liposomes containing the Wnt polypeptide are prepared by methods known in the art, such as described in Eppstein et al., *Proc. Natl. Acad. Sci. USA* 82:3688–3692 (1985); Hwang et al., *Proc. Natl. Acad. Sci. USA* 77:4030 (1980); and U.S. Pat. Nos. 4,485,045 and 4,544,545. Ordinarily, the liposomes are the small (about 200–800 Angstroms) unilamelar type in which the lipid content is greater than about 30 mol.% cholesterol, the selected proportion being adjusted for the optimal Wnt polypeptide therapy. Liposomes with enhanced circulation time are disclosed in U.S. Pat. No. 5,013,556.

For the prevention or treatment of disease, the appropriate dosage of Wnt polypeptide will depend on the type of disease to be treated, as defined above, the severity and course of the disease, whether the antibodies are administered for preventive or therapeutic purposes, previous therapy, the patient's clinical history and response to the Wnt polypeptide, and the discretion of the attending physician. The Wnt polypeptide is suitably administered to the patient at one time or over a series of treatments.

Depending on the type and severity of the disease, about 1 μg/kg to 15 mg/kg of Wnt polypeptide is an initial candidate dosage for administration to the patient, whether, for example, by one or more separate administrations, or by continuous infusion. A typical daily dosage might range from about 1 μg/kg to 100 μg/kg (e.g. 1–50 μg/kg) or more, depending on the factors mentioned above. For example, the dose may be the same as that for other cytokines such as G-CSF, GM-CSF and EPO. For repeated administrations over several days or longer, depending on the condition, the treatment is sustained until a desired suppression of disease symptoms occurs. However, other dosage regimens may be useful. The progress of this therapy is easily monitored by conventional techniques and assays.

When one or more cytokines are co-administered with the Wnt polypeptide, lesser doses of the Wnt polypeptide may be employed. Suitable doses of a cytokine are from about 1 μg/kg to about 15 mg/kg of cytokine. A typical daily dosage of the cytokine might range from about 1 μg/kg to 100 μg/kg (e.g. 1–50 μg/kg) or more. For example, the dose may be the same as that for other cytokines such as G-CSF, GM-CSF and EPO. The cytokine(s) may be administered prior to, simultaneously with, or following administration of the Wnt polypeptide. The cytokine(s) and Wnt polypeptide may be combined to form a pharmaceutically composition for simultaneous administration to the mammal. In certain embodiments, the amounts of Wnt polypeptide and cytokine are such that a synergistic repopulation of blood cells (or synergistic increase in proliferation and/or differentiation of hematopoietic cells) occurs in the mammal upon administration of the Wnt polypeptide and cytokine thereto. In other words, the coordinated action of the two or more agents (i.e. the Wnt polypeptide and cytokine(s)) with respect to repopulation of blood cells (or proliferation/differentiation of hematopoietic cells) is greater than the sum of the individual effects of these molecules.

Therapeutic formulations of Wnt polypeptide are prepared for storage by mixing Wnt polypeptide having the desired degree of purity with optional physiologically acceptable carriers, excipients, or stabilizers (*Remington's Pharmaceutical Sciences*, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween®, Pluronics™ or polyethylene glycol (PEG).

The Wnt polypeptide also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles, and nanocapsules), or in macroemulsions. Such techniques are disclosed in *Remington's Pharmaceutical Sciences,* supra.

Wnt polypeptide to be used for in vivo administration must be sterile. This is readily accomplished by filtration through sterile filtration membranes, prior to or following lyophilization and reconstitution. Wnt polypeptide ordinarily will be stored in lyophilized form or in solution. Therapeutic Wnt polypeptide compositions generally are placed into a container having a sterile access port, for example, an intravenous solution bag or vial having a stopper pierceable by a hypodermic injection needle.

When applied topically, the Wnt polypeptide is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the Wnt polypeptide formulated in a liquid composition may be mixed with an effective amount of a water-soluble polysaccharide or synthetic polymer such as PEG to form a gel of the properviscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the Wnt polypeptide held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400–600 with one of molecularweight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2–5%, more preferably about 3%, of the gel and the Wnt polypeptide is present in an amount of about 300–1000 mg per ml of gel.

An effective amount of Wnt polypeptide to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administerthe Wnt polypeptide until a dosage is reached that achieves the desired effect. A typical daily dosage for systemic treatment might range from about 1 µg/kg to up to 10 mg/kg or more, depending on the factors mentioned above. As an alternative general proposition, the Wnt polypeptide receptor is formulated and delivered to the target site or tissue at a dosage capable of establishing in the tissue a Wnt polypeptide level greater than about 0.1 ng/cc up to a maximum dose that is efficacious but not unduly toxic. This intra-tissue concentration should be maintained if possible by the administration regime, including by continuous infusion, sustained release, topical application, or injection at empirically determined frequencies. The progress of this therapy is easily monitored by conventional assays.

C. Non-Therapeutic Uses for the Wnt Polypeptide

Wnt nucleic acid is useful for the preparation of Wnt polypeptide by recombinant techniques exemplified herein which can then be used for production of anti-Wnt antibodies having various utilities described below.

The Wnt polypeptide (polypeptide or nucleic acid) can be used to induce proliferation and/or differentiation of cells in vitro. In particular, it is contemplated that this molecule may be used to induce proliferation of stem cell/progenitorcell populations (e.g. flASK cell populations obtained as described in Example 2 below). These cells which are to be grown ex vivo may simultaneously be exposed to other known growth factors or cytokines, such as those described herein. This results in proliferation, differentiation and/or maintenance of the cells.

In yet another aspect of the invention, the Wnt polypeptide may be used for affinity purification of Wnt receptor. Briefly, this technique involves: (a) contacting a source of Wnt receptor with an immobilized Wnt polypeptide under conditions whereby the Wnt receptor to be purified is selectively adsorbed onto the immobilized receptor; (b) washing the immobilized Wnt polypeptide and its support to remove non-adsorbed material; and (c) eluting the Wnt receptor molecules from the immobilizedWnt polypeptideto which they are adsorbed with an elution buffer. In an embodiment of affinity purification, Wnt polypeptide is covalently attaching to an inert and porous matrix (e.g., agarose reacted with cyanogen bromide). Preferred is a Wnt polypeptide immunoadhesin immobilized on a protein A column. A solution containing Wnt receptor is then passed through the chromatographic material. The Wnt receptor adsorbs to the column and is subsequently released by changing the elution conditions (e.g. by changing pH or ionic strength).

The Wnt polypeptide may be used for competitive screening of potential agonists or antagonists for binding to the cell surface receptors. Such agonists or antagonists may constitute potential therapeutics.

A preferred technique for identifying molecules which bind to the Wnt polypeptide utilizes a chimeric polypeptide (e.g., epitope tagged Wnt polypeptide or Wnt polypeptide immunoadhesin) attached to a solid phase, such as the well of an assay plate. Binding of molecules which are optionally labelled (e.g., radiolabelled) to the immobilized receptor can be evaluated.

The Wnt polypeptides are also useful as molecular weight markers. To use a Wnt polypeptide as a molecular weight marker, gel filtration chromatography or SDS-PAGE, for example, will be used to separate protein(s) for which it is desired to determine their molecular weight(s) in substantiallythe normal way. The Wnt polypeptide and other molecularweight markers will be used as standards to provide a range of molecular weights. For example, phosphorylase b (mw=97,400), bovine serum albumin (mw=68,000), ovalbumin (mw=46,000), a Wnt polypeptide (e.g., mw=38,000–42,000 depending on the coding sequence as described by Gavin et al., supra), trypsin inhibitor (mw=20,100), and lysozyme (mw=14,400) can be used as mw markers. The other molecularweight markers mentioned here can be purchased commercially from Amersham Corporation, Arlington Heights, Ill. The molecular weight markers are generally labeled to facilitate detection thereof. For example, the markers may be biotinylated and following separation can be incubated with streptavidin-horseradishperoxidase so that the various markers can be detected by light detection.

The purified Wnt polypeptide, and the nucleic acid encoding it, may also be sold as reagents for mechanism studies of Wnt polypeptide and its receptor, to study the role of the Wnt polypeptide and Wnt receptor in normal growth and development, as well as abnormal growth and development, e.g., in malignancies, or in diseases or disorders.

D. Wnt Polypeptide Antibody Preparation

1. Polyclonal antibodies

Potential therapeutic applications for anti-Wnt antibodies, in particular neutralizing antibodies, include the treatment of disorders, stem cell tumors and other tumors at sites of Wnt expression, including those tumors characterized by over-expressions of Wnts.

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups.

Animals are immunized against the antigen, immunogenic conjugates, or derivatives by combining 1 mg or 1 µg of the peptide or conjugate (for rabbits or mice, respectively) with 3 volumes of Freund's complete adjuvant and injecting the solution intradermally at multiple sites. One month later the animals are boosted with ⅕ to ¹/₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

2. Monoclonal antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., *Nature* 256:495 (1975), or may be made by recombinant DNA methods (Cabilly et al., supra).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, *J. Immunol.*, 133: 3001 [1984]); Brodeur et al., *Monoclonal Antibody Production Techniques and Applications*, pp. 51–63 (Marcel Dekker, Inc., New York, [1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subdloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in an animal.

The monoclonal antibodies secreted by the subdlones are suitably separated from the culture medium, ascites fluid, or serum by conventional immunoglobulin purification procedures such as, for example, protein A-Sepharose®, hydroxylapatte chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5: 256–262 [1993] and Plückthun, *Immunol. Revs.*, 130: 151–188 [1992].

In a further embodiment, antibodies or antibody fragments can be isolated from antibody phage libraries generated using the techniques described in McCafferty et al., *Nature* 348: 552–554 [1990]. Clackson et al., *Nature*, 352: 624–628 [1991] and Marks et al., *J. Mol. Biol.*, 222: 581–597 [1991] describe the isolation of murine and human antibodies, respectively, using phage libraries. Subsequent publications describe the production of high affinity (nM range) human antibodies by chain shuffling (Mark et al., *Bio/Technology*, 10: 779–783 [1992]), as well as combinatorial infection and in vivo recombinationas a strategy for constructing very large phage libraries (Waterhouse et al., *Nuc. Acids. Res.*, 21: 2265–2266 [1993]). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (Cabilly et al., supra; Morrison, et al., *Proc. Nat. Acad. Sci. USA* 81: 6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3. Humanized and human antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321:522–525 (1986); Riechmann et al., Nature, 332: 323–327 [1988]; Verhoeyen et al., Science, 239: 1534–1536 [1988]), by substituting rodent CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151: 2296 [1993]; Chothia et al., J. Mol. Biol., 196: 901 [1987]). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89: 4285 [1992]; Presta et al., J. Immnol., 151: 2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiarto those skilled in the art. Computer-programs are available which illustrate and display probable three-dimensional conformational structures of selected candidate immunoglobulin sequences. Inspection of these displays permits analysis of the likely role of the residues in the functioning of the candidate immunoglobulin sequence, i. e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

Alternatively, it is now possibleto producetransgenicanimals (e.g., mice) that are capable, upon immunization, of producing a full repertoire of human antibodies in the absence of endogenous immunoglobulin production. For example, it has been described that the homozygous deletion of the antibody heavy-chainjoining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 [1993]; Jakobovits et al., Nature, 362: 255–258 [1993]; Bvuggermann et al., Year in Immuno., 7: 33 [1993]. Human antibodies can also be produced in phage- display libraries (Hoogenboom et al., J. Mol. Biol., 227: 381 [1992]; Marks et al., J. Mol. Biol., 222: 581 [1991]).

4. Bispecific antibodies

Bispecific antibodies (BsAbs) are antibodies that have binding specificities for at least two different antigens. BsAbs can be used as tumor targeting or imaging agents and can be used to target enzymes or toxins to a cell possessing the Wnt polypeptide. Such antibodies can be derived from full length antibodies or antibody fragments (e.g. $F(ab')_2$ bispecific antibodies). In accordance with the present invention, the BsAb may possess one arm which binds the Wnt polypeptide and another arm which binds to a cytokine or another cytokine receptor (or a subunit thereof) such as the receptors for TPO, EPO, G-CSF, IL-4, IL-7, GH, PRL; the $\alpha$ or $\beta$ subunits of the IL-3, GM-CSF, IL-5, IL-6, LIF, OSM and CNTF receptors; or the $\alpha$, $\beta$ or $\gamma$ subunits of the IL-2 receptor complex.

Methods for making bispecific antibodies are known in the art. Traditional production of full length bispecific antibodies is based on the coexpression of two immunoglobulin heavy chain-light chain pairs, where the two chains have different specificities (Milstein et al., Nature 305:537–540 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published May 13, 1993, and in Traunecker et al., EMBO J., 10: 3655–3659 [1991].

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach,.the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690 published Mar. 3, 1994. For further details of generating bispecific antibodies see, for example, Suresh et al., *Methods in Enzymology* 121: 210 [1986].

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/20373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. The following techniques can also be used for the production of bivalent antibody fragments which are not necessarily bispecific. According to these techniques, Fab'-SH fragments can be recovered from *E. coli,* which can be chemically coupled to form bivalent antibodies. Shalaby et al., *J. Exp. Med.,* 175: 217–225 [1992] describe the production of a fully humanized BsAb F(ab')$_2$ molecule. Each Fab' fragment was separately secreted from *E. coli* and subjected to directed chemical coupling in vitro to form the BsAb. The BsAb thus formed was able to bind to cells overexpressingthe HER2 receptor and normal human T cells, as well as triggerthe lytic activity of human cytotoxic lymphocytes against human breast tumor targets. See also Rodrigues et al., *Int. J. Cancers* (Suppl.), 7: 45–50 [1992]. Various techniques for making and isolating bivalent antibody fragments directly from recombinant cell culture have also been described. For example, bivalent heterodimers have been produced using leucine zippers. Kostelnyet al., *J. Immunol.,* 148(5): 1547–1553 [1992]. The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Holliger et al., *Proc. Natl. Acad. Sci. USA,* 90: 6444–6448 [1993] has provided an alternative mechanism for making BsAb fragments. The fragments comprise a heavy-chainvariable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making BsAb fragments by the use of single-chain Fv (sFv) dimers has also been reported. See Gruber et al., *J. Immunol.* 152:5368 (1994).

E. Articles of Manufacture

In another embodiment of the invention, an article of manufacture containing materials useful for the treatment of the conditions described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the Wnt polypeptide. The label on, or associated with, the container indicates that the composition is used for treating the condition of choice. The article of manufacture may further comprise a second container holding a cytokine for co-administration with the Wnt polypeptide. Further container(s) may be provided with the article of manufacturewhich may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

F. Non-Therapeutic Uses for Antibodies to Wnts

Wnt polypeptide antibodies are also useful as affinity purification agents. In this process, the antibodies against Wnts are immobilized on a suitable support, such a Sephadex® resin or filter paper, using methods well known in the art. The immobilized antibody then is contacted with a sample containing the Wnts to be purified, and thereafter the support is washed with a suitable solvent that will remove substantiallyall the material in the sample except the Wnts, which is bound to the immobilized antibody. Finally, the support is washed with another suitable solvent, such as glycine buffer, pH 5.0, that will release the Wnt polypeptide from the antibody.

Wnts antibodies may also be useful in diagnostic assays for Wnt polypeptide, e.g., detecting its expression in specific cells, tissues, or serum. For diagnostic applications, antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase or horseradish peroxidase.

Any method known in the art for separately conjugating the polypeptide variant to the detectable moiety may be employed, including those methods described by Hunter et al., *Nature,* 144: 495–496 [1962]; David et al., *Biochemistry,* 13: 1014 [1974]; Pain et al., *J. Immunol. Meth,* 40: 219 [1981]; and Nygren, *J. Histochem. and Cytochem.,* 30: 407 [1982].

The antibodies of the present invention may be employed in any known assay method, such as competitive binding assays, direct and indirect sandwich assays, and immunoprecipitation assays. *Zola, Monoclonal Antibodies: A Manual of Techniques,* pp.147–158 (CRC Press, Inc., 1987).

Competitive binding assays rely on the ability of a labeled standard to compete with the test sample analyte for binding with a limited amount of antibody. The amount of Wnt polypeptide in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,1 10. The second antibody may itself be labeled with a detectable moiety (direct sandwich assays) or may be measured using an anti-immunoglobulinantibody that is labeled with a detectable moiety (indirect sandwich assay). For example, one type of sandwich assay is an ELISA assay, in which case the detectable moiety is an enzyme.

III. Experimental

Below are examples of specific embodiments for carrying out the present invention. The examples are offered for illustrative purposes only, and are not intended to limit the scope of the present invention in any way.

The disclosures of all publications, patents and patent applications cited herein, whether supra or infra, are hereby incorporated by reference in their entirety.

EXAMPLE 1

Screening of Wnt Genes in Cells and Cell Lines

Both hematopoieticstem cell populationsand stromal cell lineswhich support hematopoietic stem/progenitor cell growth were surveyed for Wnt expression by RT-PCR analysis. For these experiments, fetal liver and bone marrow hematopoietic stem/progenitor cell populations were prepared essentially as described (see, e.g., Example 2A of U.S. Ser. No. 08/222,299, corresponding PCT/US95/03718; and Zeigler et al., *Blood,* 84: 2422–2430 [1994].

Briefly, day 14–15 fetal livers were made into a single cell suspension and AA4$^+$ cells were positively selected by immunoadherentpanning using the AA4$^+$ antibodies purified from hybridoma supernatents as described by Zeigleret al., supra. Sca$^+$ c-kit$^+$ dual positive cells were recovered from the AA4$^+$ cell population by flow cytometric sorting using the Ly6 A/E phycoerythrin conjugate (Pharmingan, San Diego, Calif.) to recover Sca$^+$ cells and using fluorescein conjugated antibodies to c-kit (also from Pharmingan). Lin$^{lo}$Sca$^+$ bone marrow cells were recovered by magnetic bead depletion (Dynal, Inc., Great Neck, N.J.; Ploemacheret al., *Blood,* 74: 2755–2763 [1989]) of lineage-antigen expressing cells from total bone marrow and selection of Lin$^{lo}$Sca$^+$ cells by flow cytometric sorting using Lin cocktail antibodiesfrom Caltag (South Francisco, Calif.) as described (see, Example 2A of U.S. Ser. No. 08/222,299, corresponding PCT/US95/03718; and Zeigler et al., supra.

For the RT-PCR analysis of these cell subpopulations, PCRs were carried out with Taq polymerase (Cetus) on AA4$^+$Sca$^+$ cDNA or a 7-4 cell line cDNA library using each sense primer (LL1–7) with the Wnt3 antisense primer (sense primers: LL1 5' CAA GAG TGC AAA TGC CAC GGG ATG TCC GGC TCC TGC 3'(SEQ ID NO: 2) LL2 5' CAA GAG TGC AAA TGC CAC GGG GTG TCC GGC TCC TGC 3'(SEQ ID NO: 3); LL3 5' CTC AAG TGC AAA TGC CAC GGG CTA TCT GGC AGC TAGT 3'(SEQ ID NO: 4); LL 4 5' GTG GAG TGC AAG TGC CAC GGG GTG TCC GGC TCC TGC 3' (SEQ ID NO: 5); LL5 5' GTA GCC TGT AAG TGC CAT GGA GTG TCT GGC TCC TGT 3' (SEQ ID NO: 6); LL6 5' ACC GGG TGT AAG TGC CAT GGG CTT TCG GGT TCC TGC 3' (SEQ ID NO: 7); LL7 5' CTG GAG TGT AAG TGC CAT GGT GTG TCA GGC TCC TGT 3' (SEQ ID NO: 8); antisense primer "Wnt3" 5' GCC (C/G)CG GCC (G/A)CA (G/A)CA CAT3' (SEQ ID NO: 9)).

Additional PCRs were performed with the primer Wnt1a (5'(G/C)TG GA(A/G) TG(C/T) AA(A/G) TG(C/T) CAT 3' (SEQ ID NO: 10) and Wnt2a5' (A/G)CA (A/G)CA CCA (A/G)TG (A/G)AA3' (SEQ ID NO: 11). PCR products were cloned as a blunt-ended fragments into SmaI-linearized pGEM®7 (Promega) and screened for Wnt sequences by hybridization with the oligonucleotides Liem1 5' GAC CTG GTG TAC 3' (SEQ ID NO: 12) or Liem2 5' TG(T/C) TG(T/C) GGC CG(G/C) GGC 3' (SEQ ID NO: 13). This analysis was confirmed using the following specific primers for Wnt-5a and Wnt-10b, using Wnt-3a as a negative control: Wnt-3a (wn3a.2,5' CAG CCC AGG CGT CCG CGC TC3' (SEQ ID NO: 14); wn3a.3, 5'GGA ATG AAC CCT GCT CCC GT 3' (SEQ ID NO: 15), Wnt-5a (wn5a1050, 5' CGC GCC CCA AGG ACC TGC CTC G 3' (SEQ ID NO: 16); wn5ar1499, 5' GCG AGC CAG TGC TCT CGT TGC G 3' (SEQ ID NO: 17); Wnt-10b (W10.1, 5' AAA CCT GAA GCG GAA GTG CAA ATG C 3' (SEQ ID NO: 18); w10.3, 5' GCT CAC CTT CAT TTA CAC ACA TTG A 3' (SEQ ID NO: 19).

These experiments detected only Wnt-5a and Wnt-10b in fetal liver AA4$^+$ Sca$^+$ cells. Similar experiments were performed on a fetal liver stromal cell line, 7-4 (prepared as described in co-pending and coassigned U.S. patent application Ser. No. 08/222,299; corresponding PCT/US95/03718 (WO95/27062); and Zeigleret al., supra), where expression of only Wnt-5a was detected. Thus highly enriched stem/progenitorcells and stromal cells that support their expansion were found to express Wnts.

These observations were extended by RT-PCR on mRNAs from the highly enriched fetal liver stem cell population AA4$^+$ Sca$^+$ kit$^+$ ("flASK" cells, prepared as described in co-pending and coassigned U.S. patent application Ser. No. 08/222,299; corresponding PCT/US95/03718 (WO95/27062); and Zeigleret al., supra, using the antibody reagents described above). Wnt-5a, and Wnt-10b, but not Wnt-3a, were detected in the flASK cells. Moreover, the lack of Wnt-3a expression in flASK cells demonstrated that, at the level of detection of the RT-PCR assays, hematopoietic stem cells express only a subset of the possible Wnt genes.

In additional experiments, Wnt-5a and Wnt-10b mRNAs were shown to be expressed in the stem cell populationsAA4$^+$, AA4$^+$Sca$^+$flk2$^+$ and AA4$^+$Sca$^+$flk2 (Zeigleret al.,supra). Importantly, the expression of these Wnt mRNAs in three different hematopoietic stem/progenitor cell subsets, each purified independently by virtue of c-kit or flk2 expression, and all three cell subsets capable of long term engraftment of lethally irradiated animals, strongly suggested a role for these ligands in the local microenvironmentof the hematopoietic stem/progenitor cell. The expression of Wnt-5a in a fetal liver stromal cell line, 7-4, described above, and of Wnt-5a and Wnt-10b mRNAs in more mature (AA4$^-$) fetal liver hematopoietic cells further suggested (i) that much of the fetal liver hematopoietic microenvironment, as well as hematopoietic stem/progenitor cells, could potentially serve as a source of Wnts and (ii) that the expression of Wnt on these cells could allow for Wnt-mediated paracrine or autocrine regulation of the differentiation of these cells.

EXAMPLE 2

Analysis of Wnts in Hematopoiesis

A. Expansion of Hematopoietic Stem/Progenitor Cells Stimulated by Conditioned Media From Wnt-Transfected Cells An in vitro stroma-free suspension culture system was developed to study the function of Wnts on highly enriched hematopoieticstem/progenitor cell populations prepared as described in Example 1. For these experiments, suspension culture of the enriched sorted cells was carried out in 24 well Costar dishes with 5000 cells/well seeded into 0.5 ml of HSC media and cultured at 37° C. with 5% $CO_2$. HSC media contained 50% F12/50% low glucose DMEM, 10% heat-treated fetal bovine serum (Hyclone), 1 mM Glutamine, and murine kit ligand (KL) as indicated (R&D Systems). Conditioned media from 293 cells transfected with cloned Wnt genes was added at the time of plating. Specifically, Wnt-5a cDNAs were cloned from a 7-4 fetal liver stromal cell line cDNA library and Wnt-10b cDNAs were cloned using RT-PCR from flASK cell mRNAs. For the molecular cloning of Wnt cDNAs, poly A$^+$ RNA was prepared by the Fast Track method (Invitrogen) and cDNA was made by denaturing PolyA$^+$ RNA and dT$_{18}$ primers in the presence of 0.1 M methyl mercuric hydroxide, followed by quenching with 20 mM beta-mercaptoethanol and extension in 20 $\mu$l total with Superscript reverse transcriptase as recommended (Gibco).

A Wnt-5a PCR fragmentwas used to screen a cDNA library made from the 7-4 cell line and ligated into the pSPORT-1 vector (Gibco). The Wnt-5a coding region was sequenced from one clone, Wnt5a.13.pSPORT-1, and the predicted amino acids matched those previously reported (Gavin et al., *Genes and Dev.*, 4: 2319–2332 [1990]) except for (H207>Y). A Wnt-10b cDNA was cloned by RT-PCR from flASK cells using primers wn10b.5ri (5'GGA ATT CCG GGC TTC GAC ATG CTG GAG GA 3') and wn10b.3kpn (5'GGG GTA CCC CAG GCT CAC CTT CAT TTA CAC A 3'), and cloned into pGEM7. The predicted coding sequence matched exactly to that reported elsewhere (Lee et al., *Proc. Natl. Acad. Sci. USA*, 92: 2268–2272 [1995]).

For overexpression of murine Wnts in mammalian cells and the preparation of conditioned media (CM) from the cells containing Wnt gene products, the Wnt-1, Wnt-5a, and Wnt-10b cDNAs thus obtained were cloned into as EcoRI/Hind III fragments into an expression vector pRK5tkneo (Holmes, *Science*, 253: 1278–1280 11991]). For production of CM, 293 cells were transfected by the calcium phosphate method (Gorman, *DNA Cloning: A Practical Approach*, IRL, Wash., D.C. [1985]), media was collected after at least 48 hours, centrifuged at 3,000(SEQ ID NO: 20)×g, and sterile filtered. In most experiments using CM, the CM was added to 5–10% final concentration. In preliminary experiments, most of the known cytokines failed to support the survival of flASK cells in suspension cultures when added as single factors in the presence of 10% fetal bovine serum (see, e.g., Bodine et al., *Blood,* 78: 914–920 [1991]). The addition of KL at 100 ng/ml, however, provided a potent stimulus for cell survival and proliferation of granulocytic progenitors (Anderson et al., *Cell,* 63: 235–243 [1990]; Zsebo et al., *Cell,* 63: 195–201 [1990]. Interestingly, control 293 CM provided an approximately 2-fold stimulatory activity when added to suspension cultures with KL. The addition of conditioned media (CM) from 293 cells transfected with a Wnt-5a CDNA evoked a 2–3 fold greater expansion than control CM.

The presence of Wnt-5a protein in the CM from transfected cells was confirmed by immunoprecipitations and Western blotting. For these experiments, a chimeric Wnt-5a gene was made encoding the first 55 amino acids (AA) of herpes simplex virus glycoprotein D followed by Wnt-5a AA 38–379 in gDCT-1pRK5b (Pennica et al., *Proc. Natl. Acad. Sci. USA,* 92: 1142–1146 [1995]). The control vector used in experiments involving gDWnt5a was made from gDCT-1pRK5b by excising the CT-1 cDNA as a XhoI-Xbal fragment, filling in the overhanging nucleotides, and closing the gDpRK5b vector with T4 DNA ligase (Collaborative Research). The resulting construct was expected to encode the first 54 AA of gD followed by D stop. A fragment encoding six histidine residues was appended in-frame to the carboxy terminus of Wnt-5a in the gDpRK5b vector by PCR.

For immunoprecipitation experiments for the analysis of Wnt expression by transfected cells, 293 cells transfected with gDpRK5b or gDWnt5apRK5b were labeled in 100 $\mu$Ci [$^{35}$S]methionine/[$^{35}$S]cysteine (Amersham), lysed, and proteins were precipitated with the 5B6 mAb plus protein A Sepharose® (Pharmacia). The precipitates were washed, electrophoresed, and fluorographed according to standard methods.

For comparison, the potent cytokines IL-3 and GM-CSF added as single factors to cultures with KL evoked a 1.5–2 fold greater expansion than controls. Further experiments revealed that titration of KL to 25 ng/ml provided a lower expansion in cell number, but the cultures displayed a reduced level of granulocytic proliferation/differentiation. Addition of Wnt-1, Wnt-5a, and Wnt-10b CM to the suspension cultures of flASK cells plus 25 ng/ml KL stimulated cell proliferation 7, 8, and 11-fold (respectively) over that of control CM after 7 days in culture as shown in FIG. 1. A synergistic effect between KL and Wnts was evident since Wnt CM alone triggered very little cell survival/proliferation. Thus far, Wnt-1 expression has not been detected in the hematopoietic system, however, Wnt-1 CM was active in this assay. These results demonstrate the potential for distinct signaling pathways from several Wnt ligands leading to a similar response of hematopoietic cells or the presence of a common Wnt receptor in hematopoietic stem/progenitor cells.

B. Maintenance of the Blast Cell Phenotype and Foci Formation of Hematopoietic Progenitor Cells Enhanced by Wnts In mice, Wnts are essential for the development of several primitive cell types and in Xenopus they are thought to be involved in cell fate determination. The role of Wnts was evaluated on the differentiation potential of pluripotent hematopoietc stem/progenitor cells by examining the morphology of cultured cells in cytostained preparations. For the cytospin analysis, cells were grown in suspension culture as described above, spun onto a glass slide and then stained with Wright Geimsa to reveal hematopoietic cell types and morphology. For these experiments, cytospin analysis of flASK cells was performed with cytospin preparations of (A) flask cells immediately after cell sorting, (B) flASK cells after suspension culture in control CM plus 25 ng/ml KL, and (C) flASK cells after suspension culture in Wnt-5a CM plus KL. Although addition of KL to the suspension cultures was essential, even in reduced concentrations, the effect of KL alone was to promote the differentiation and proliferation of granulocytic cells from HSCs compared to freshly isolated flASK cells. However, cells cultured in Wnt-5a or Wnt-10b CM or partially purified recombinantWnt-5a (see Section C below) generally gave rise to a greater diversity of cell lineages with less commitmenttowards granulocytic lineages. Myeloid cells (macrophages and neutrophils), megakaryocytes, and early erythroid cells, were observed by cytospin analysis of suspension cultures after treatment with Wnt-5a CM. Notably, the ratio of primitive blasts to differentiated mononuclear cells was elevated over 4-fold (29%±3.4 compared to 7%±0.8 for the control) in cultures with recombinant Wnt-5a. The effect of Wnts plus KL was to promote extensive cell expansion, that is the net increase in cell number from the initial HSC inoculum, while also maintaining a 4 fold greater proportion of cells with a primitive blast cell morphology.

Wnts have been implicated in the regulation of cell adhesion systems, and it has been proposed that cell-cell interactions may be important in cell fate determination, (Hinck et al., *J. Cell. Biol*,124: 729–741 [1994]; Peiffer; *Development Suppl.,* 163–176 [1993]). During the first 4–5 days of suspension culture in Wnt CM, a dramatic increase in the number of loosely adherent cell aggregates or adherent hematopoietic 'foci' were observed. To analyze the spatial organization and morphology of these foci, flASK cells in HSC media with 25 ng/ml murine KL were plated onto Lab-Tek glass chamber slides (NUNC, Naperville, Ill.) coated with 50 mg/ml of human plasma fibronectin (Gibco), cultured for 4–5 days in control CM plus 25 ng/ml KL, and (E) Wnt-5a CM (gDWnt5a) plus 25 ng/ml KL, and then cytostained in situ to preserve the intercellular organization of the foci. Fibronectin was chosen as an adhesive substrate in this assay since it can mediate adhesion of CFU-S progenitors in vitro (Williams et al., *Nature,* 352: 438–441 [1991]). After 3–5 days in culture, clusters of 5 to more than 30 blasts with low cytoplasm to nucleus ratios were typically found in contact with one or more underlying adherent myeloid cells when the control culture in preparation D was compared with Wnt-5a treated cells in preparation E). The formation of these blast cell foci was dramatically enhanced in response to Wnt CM and suggested a role for Wnts in cell expansion via the regulation of cellular interactions.

In light of the enhanced proliferation and cell-cell adhesion of cells cultured in Wnt CM, the lineage phenotypes and adhesion systems of the cultured cells were analyzed by flow cytometry. For cell analysis and sorting experiments, phycoerythrin-conjugated antibodies (Ly6A/E, TER-119, CD14), fluorescein-conjugated antibodies (c-kit, CD13, CD31, CD44, CD45, CD49d, CD49e, GR1, VCAM-1, ICAM-1, L-selectin), CD11a, and CD29 antibodies were purchased from Pharmingen; phycoerythrin-conjugated Mac-1, fluorescein-conjugated antibodies (CD4, CD8a, and B220), and all secondary and Lin cocktail antibodies were purchased from Caltag.

The flASK cells were cultured in gDWnt5a CM (Wnt CM) or gD CM (control CM) for 7 days and scored for the expression of cell surface antigens. The expression of antigens found on mature hematopoietic cells (CD4, CD8a, CD13, CD14, B220, VCAM-1, and integrin beta-7) was low or negative on freshly sorted flASK cells and remained at similar levels after culture. Little or no change was observed in either condition for expression of CD11a, CD29, CD31, CD44, CD45, CD49d, CD49e, GR1, L-selectin, ICAM-1. Cultures supplied with Wnt-5a CM did, however, have an increase in the number of cells that were Sca$^+$ (154±22.6%), c-kit$^+$ (158±36%), Sca$^+$ c-kit$^+$ (131±9.4%), or Ter119$^+$ (237±25.8%). These cell surface antigen profiles compared well with the cytospin analysis and strengthened the finding that Wnts plus KL promote the maintenance of a greater proportion of primitive blast cells than KL alone during the ex vivo culture of HSCs.

C. Requirement of Secreted Wnt Protein in Wnt-Conditioned Media for Proliferation of Hematopoietic Stem/Progenitor Cells Several approaches were taken to distinguish a direct role of Wnts on HSCs from the alternative that Wnts stimulate the production of other growth factors in the transfected cells. Antibody depletion experiments were carried out to confirm that the proliferation was mediated by secreted Wnt proteins present in the media. An epitope-tag was engineered onto Wnt-5a to enable depletion with readily available antibody reagents. Chimeric proteins were constructed as described in Section A above that encoded the signal sequence and an N-terminal domain of the herpes virus glycoprotein D (gD) followed by Wnt-5a (gDWnt5a, gDWnt5aHis$_6$. Transfection of the gDWnt5a construct into 293 cells directed the expression of a 47–49kD polypeptide which was specifically immunoprecipitated from lysates by a mAb (5B6) recognizing an N-terminal epitope of gD. Immunodepletion experiments were conducted to remove the Wnt protein produced by the 293 transfected cells (gDWnt5apRK5b or control gDpRK5b) from the CM with the mAb5B6. Incubation of gDWnt5aHis$_6$ CM in mAb 5B6 bound to protein A or coupled to controlled-poreglass (5B6-CPG) reduced cell expansion to control values. Collectively, these data indicate that secreted Wnts mediated the observed cell expansions in vitro. To test whether Wnts could directly stimulate cell proliferation, we evaluated the activity of partially-purified Wnt-5a protein in the suspension culture assay. Preliminary experiments showed that cell extracts provided a richer source of Wnt-5a protein than CM. For the purification of gD.Wnt5a.His$_6$, stable lines of CHOdp12cells (DHFR cells, see, e.g., Bennett et al., *J. Biol. Chem.,* 266: 23060 [1991]) that had been transfected with a DHFR$^+$ plasmid gD.Wnt5a.His$_6$pSVi.del.d were selected and maintained in glutathione-S-transferase (GHT)-free media. Extracts were made from gD.Wnt5a.His$_6$ CHO cells as follows. Cells were lysed in 50 mM Triethanolamine, 100 mM NaCl, 0.4% SDS, 1% PMSF, and 2% Triton® X-100. Purification of gD.Wnt5a.His$_6$ from the lysate was accomplished by binding of the gD epitope to 5B6-CPG, extensive washing in PBS, and acid elution. The eluate was neutralized, dialyzed against PBS, and refolded in 8 M urea. The refolded Wnt-5a protein was diluted in HSC media so that concentration of urea was less than 60 mM Wnt-5a in the stem cell suspension culture assay.

Gel analysis revealed that the protein migrated as a 47–49kD monomer under reducing conditions. When added to the suspension culture assay, recombinant Wnt-5a protein was found to stimulate cell expansion by 5-fold at approximately 40–80 ng/ml or 1–2 nM.

D. Stimulation of Total CFC Expansion of Hematopoietic Progenitor Cells by Wnt Protein An important measure of hematopoietic progenitor cells is the ability to form colonies in semi-solid media in response to lineage-specific cytokines and multilineage colony-stimulating factors. Since the addition of Wnts plus KL to flASK cell cultures increased the proportion of cells with a primitive morphology and cell surface phenotype, experiments were performed to analyze whether the number of highly proliferative colony-forming cells had increased as well. The frequency of colony forming cells (CFCs) in flASK cell cultures was examined by measuring colony formation of cells replated into myeloid methylceliulose containing a combination of cytokines (KL, IL-3, IL-6, and Epo) and Wnt CM or control CM. For the colony assay experiments, methylcellulose cultures were initiated in 35 mM plates with 1000 cells in 1.0 ml complete myeloid methylcellulose (Stem Cell Technologies, Inc.) or in B-cell conditions consisting of base methylcellulose containing 50 ng/ml murine KL and 50 ng/ml murine IL-7 (R&D Systems). Conditioned media was added at the time of plating. Plates were read at day 12 after plating. After suspension culture, the total CFCs derived from 1000 cells in the initial culture inoculum was 3-fold greater in Wnt-5a CM than control CM. Moreover, when cells were harvested from day 12 myeloid methylcellulose cultures and replated, the cumulative expansion of cells brought forth by Wnt-5a CM was over 235 fold greater than for control CM, largely due to the inability of cells grown in control CM to efficiently replate. These results provide compelling functional evidence that secreted Wnts enhance the survival/proliferation of multipotent hematopoietic progenitors in suspension culture and can directly stimulate the expansion of primitive, highly proliferative colony forming cells.

Colony formation of freshly isolated fetal liver AA4$^+$ Sca$^+$ cells in Wnt-5a CM was also tested. Wnt-5a CM stimulated colony formation approximately 3-fold in myeloid methylcellulose. In B-cell conditions, Wnt-5a CM stimulated colony formation 4-fold. Colony formation was enhanced 2-fold for bone marrow Lin$^{lo}$ Sca+ cells in myeloid and B-cell methylcellulose. Overall, these data show that Wnt CM enhances colony formation by highly enriched fetal liver and bone marrow HSCs in conditions that detect myeloid or B-cell progenitors.

E. Expansion of Hematopoietic Stem/Progenitor Cells After Transduction with a Retrovirus Bearing a Wnt Protein To further examine the direct effects of Wnt expression on HSCs, a representative Wnt protein product, Wnt-5a, was introduced via retroviral transduction. A Rous sarcoma virus-based bicistronic LNL6 vector was constructed so that Wnt-5a was placed 3' to the gag gene and LacZ was downstream of the encephalomyocarditis virus internal ribosome entry site. Specifically, for the viral construction and transduction experiments, Wnt5a.13.pSPORT-1 was digested with EcoRI/BamHl, the insert was blunted with T4 DNA Polymerase (U.S. Biochemical), and cloned into blunted BgIII/BamHl sites of the pLNL6 vector (Ghattas et al., *Mol. Cell. Biol.*, 11: 5848–5859 [1991]). Wnt5a/LNL6 or the parental LNL6 vectorwere transfected by a calcium phosphate method into BOSC 23 cells (Pear et al., *Proc. Nati. Acad. Sci. USA,* 90: 8392–8396 [1993]). Viral supernatantsfrom the transfected BOSC cells were collected after 48–72 hours and stored at −20° C and used to transduce flASK cells. Transductions of the flASK cells were carried out at 100,000 cells per ml for 48 hours in viral supernatants supplemented with the murine cytokines IL-3 (25 ng/ml), IL-6 (50 ng/ml), and KL (10 ng/ml). Transduction efficiency of cells giving rise to methylcellulose colonies was assayed by PCR analysis essentially as described in Gerard et al., *Human Gene Therapy,* 7: 343–354 [1996]. Expression of the biscistronic mRNA in transduced flASK cells was confirmed by measuring LacZ activity using the FACS-Gal method (Fiering et al., *Cytometry,* 12: 291–301 [1991]). The added cytokines IL-3, IL-6, and KL increased the transduction efficiency, which was estimated to be approximately 20% by FACS-Gal analysis 48 hours post-transduction. A potential early-acting effect of Wnt-5a on cell survival/proliferation was measured by counting cell numbers 48 hours after transduction. Wnt5a/LNL6-transduced cells expanded by almost 2-fold (FIG. 2A). Notably, this cell survival/proliferation was impressive in that an additional benefit was observed over the potent effects of the early-acting cytokines IL-3, IL-6, and KL. Culture of the Wnt5a/LNL6-transduced cells for 7 days revealed extensive proliferation compared to that of control cells (FIG. 2B). Cells from 2 day transductions were also replated into myeloid methylcellulose. Transduction with Wnt5a/LNL6 stimulated a 3-fold greater expansion of CFCs than the control vector (FIG. 2C). The efficiency of CFC transduction was estimated to be 14–47% by PCR analysis of colonies plucked from the methylcellulose cultures.

What is claimed is:

1. A method for enhancing or increasing myelopoiesis, erythropoiesis or lymphopoiesis comprising exposing hematopoietic stem/progenitor cells to an amount of isolated Wnt polypeptide effective for stimulating proliferation or differentiation of the cells.

2. The method of claim 1, wherein the cells comprise CD34+ cells.

3. The method of claim 1, wherein the cells comprise AA4+ cells.

4. The method of claim 1, wherein the cells comprise flASK cells.

5. The method of claim 1, wherein the hematopoietic stem/progenitor cells are present in cell culture.

6. The method of claim 1, wherein the cells are present in a mammal.

7. The method of claim 6, wherein the mammal is a human.

8. The method of claim 1, which enhances or increases lymphopoiesis.

9. The method of claim 1, which enhances or increases erythropoiesis.

10. The method of claim 1, which enhances or increases myelopoiesis.

11. The method of claim 1, further comprising exposing the cells to another cytokine.

12. The method of claim 11, wherein the cytokine is lineage-specific.

13. The method of claim 1, wherein the cytokine is selected from the group consisting of: thrombopoietin (TPO), erythropoietin (EPO), macrophage-colony stimulating factor (M-CSF), granulocyte-macrophage-colony stimulating factor (GM-CSF), granulocyte-colony stimulating factor (G-CSF), interleukin-1 (IL- 1), IL-1a, IL-2, IL-3, IL-4, IL-5, IL-6, IL-7, IL-8, IL-9, IL-10, IL-11, IL-12, leukemia inhibitory factor and kit ligand.

* * * * *